(12) United States Patent
Racenet et al.

(10) Patent No.: US 8,905,287 B2
(45) Date of Patent: Dec. 9, 2014

(54) DIRECTIONALLY BIASED STAPLE AND ANVIL ASSEMBLY

(71) Applicant: Covidien LP, Mansfield, MA (US)

(72) Inventors: David C. Racenet, Killingworth, CT (US); Hanspeter R. Bayer, Meriden, CT (US); Scott Nelson Cunningham, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/205,927

(22) Filed: Mar. 12, 2014

(65) Prior Publication Data

US 2014/0183243 A1   Jul. 3, 2014

Related U.S. Application Data

(63) Continuation of application No. 13/368,407, filed on Feb. 8, 2012, now Pat. No. 8,684,249, which is a continuation of application No. 13/052,289, filed on Mar. 21, 2011, now Pat. No. 8,123,101, which is a continuation of application No. 12/568,135, filed on Sep. 28, 2009, now Pat. No. 7,926,692, which is a continuation of application No. 11/981,441, filed on Oct. 31, 2007, now Pat. No. 7,611,038, which is a continuation of application No. 11/253,493, filed on Oct. 17, 2005, now Pat. No. 7,398,907, which is a continuation of application No. 09/972,594, filed on Oct. 5, 2001, now abandoned, which is a continuation-in-part of application No. 09/693,379, filed on Oct. 20, 2000, now abandoned.

(51) Int. Cl.

| A61B 17/068 | (2006.01) |
|---|---|
| A61B 17/064 | (2006.01) |
| A61B 17/072 | (2006.01) |
| A61B 17/115 | (2006.01) |
| A61B 17/32 | (2006.01) |

(52) U.S. Cl.
CPC ......... *A61B 17/0682* (2013.01); *A61B 17/0644* (2013.01); *A61B 17/068* (2013.01); *A61B 17/0684* (2013.01); *A61B 17/0686* (2013.01); *A61B 17/072* (2013.01); *A61B 17/07207* (2013.01); *A61B 17/115* (2013.01); *A61B 2017/07264* (2013.01); *A61B 2017/320052* (2013.01)
USPC .......... 227/176.1; 227/18; 227/61; 227/175.1

(58) Field of Classification Search
USPC ......... 227/19, 175.1, 176.1, 178.1, 180.1, 61; 606/139, 219
See application file for complete search history.

(56) References Cited

U.S. PATENT DOCUMENTS

| 2,008,086 A | 7/1935 | Sorenson |
|---|---|---|
| 2,122,814 A | 7/1938 | Hansen |

(Continued)

FOREIGN PATENT DOCUMENTS

| EP | 529968 | 12/1957 |
|---|---|---|
| EP | 0251444 | 1/1988 |

(Continued)

OTHER PUBLICATIONS

European Search Report for EP 10155752.8-2310 date of completion is Apr. 19, 2010 (5 pages).

(Continued)

*Primary Examiner* — Scott A. Smith

(57) ABSTRACT

An anvil assembly having a tissue contact surface and a plurality of staple pockets formed in the tissue contact surface. Each of the plurality of staple pockets including first and second staple forming cups, each of the first and second staple forming cups having an outside portion and an inside portion, the inside portion of the first and second staple forming cups being positioned in close relation to each other and the outside portion of the first and second staple forming cups being positioned in spaced relation to each other. Each of the first and second staple forming cups being defined by sidewalls and an elongated base surface, wherein upper portions of the sidewalls intersect the tissue contact surface at a line of intersection, and wherein the line of intersection is curved along a majority of its length between the outside portion and the inside portion of each of the staple forming cups.

18 Claims, 35 Drawing Sheets

(56) References Cited

U.S. PATENT DOCUMENTS

| | | |
|---|---|---|
| 2,128,443 A | 8/1938 | Vogel |
| 2,153,874 A | 4/1939 | Posnack |
| 3,490,675 A | 1/1970 | Green et al. |
| 3,494,533 A | 2/1970 | Green |
| 3,499,591 A | 3/1970 | Green |
| 3,564,663 A | 2/1971 | Roberts |
| 4,275,813 A | 6/1981 | Noiles |
| 4,281,785 A | 8/1981 | Brooks |
| 4,304,236 A | 12/1981 | Conta |
| 4,319,576 A | 3/1982 | Rothfuss |
| 4,383,634 A | 5/1983 | Green |
| 4,407,286 A | 10/1983 | Moiles et al. |
| 4,425,915 A | 1/1984 | Ivanov |
| 4,427,008 A | 1/1984 | Transue |
| 4,438,769 A | 3/1984 | Pratt et al. |
| 4,454,875 A | 6/1984 | Pratt et al. |
| 4,467,805 A | 8/1984 | Fukuda |
| 4,485,816 A | 12/1984 | Krumme |
| 4,520,817 A | 6/1985 | Green |
| 4,531,522 A | 7/1985 | Bedi et al. |
| 4,534,351 A | 8/1985 | Rothfuss et al. |
| 4,548,202 A | 10/1985 | Duncan |
| 4,550,870 A | 11/1985 | Krumme et al. |
| 4,589,582 A | 5/1986 | Bilotti |
| 4,607,638 A | 8/1986 | Crainich |
| 4,632,290 A | 12/1986 | Green et al. |
| 4,724,839 A | 2/1988 | Bedi et al. |
| 4,741,336 A | 5/1988 | Failla et al. |
| 4,747,531 A | 5/1988 | Brinkerhott et al. |
| 4,767,044 A | 8/1988 | Green |
| D297,764 S | 9/1988 | Hunt et al. |
| 4,787,387 A | 11/1988 | Burbank, III et al. |
| 4,805,823 A | 2/1989 | Rothfuss |
| 4,878,608 A | 11/1989 | Mitsuhashi |
| 4,887,601 A | 12/1989 | Richards |
| 4,955,898 A | 9/1990 | Matsutani et al. |
| 4,978,049 A | 12/1990 | Green |
| 5,007,921 A | 4/1991 | Brown |
| 5,026,390 A | 6/1991 | Brown |
| 5,111,987 A | 5/1992 | Moeinzadeh et al. |
| 5,173,133 A | 12/1992 | Morin |
| 5,219,353 A | 6/1993 | Garvey, III et al. |
| 5,221,036 A | 6/1993 | Takase |
| 5,222,975 A | 6/1993 | Crainich |
| 5,242,457 A | 9/1993 | Akopov et al. |
| 5,246,443 A | 9/1993 | Mai |
| 5,342,396 A | 8/1994 | Cook |
| 5,350,400 A | 9/1994 | Esposito et al. |
| 5,354,306 A | 10/1994 | Garvey, III et al. |
| 5,366,479 A | 11/1994 | McGarry |
| 5,395,030 A | 3/1995 | Kuramoto et al. |
| 5,413,584 A | 5/1995 | Schulze |
| 5,415,334 A | 5/1995 | Williamson, IV et al. |
| 5,445,648 A | 8/1995 | Cook |
| 5,454,814 A | 10/1995 | Comte |
| D364,462 S | 11/1995 | Michelson |
| 5,480,089 A | 1/1996 | Blewett |
| 5,486,187 A | 1/1996 | Schenck |
| 5,489,058 A | 2/1996 | Plyley et al. |
| 5,497,933 A | 3/1996 | Defonzo et al. |
| D378,409 S | 3/1997 | Michelson |
| 5,630,541 A | 5/1997 | Williamson, IV et al. |
| 5,632,432 A | 5/1997 | Schulze et al. |
| 5,702,048 A | 12/1997 | Eberlin |
| 5,725,554 A | 3/1998 | Simon et al. |
| 5,732,872 A | 3/1998 | Bolduc et al. |
| 5,735,444 A | 4/1998 | Wingert |
| 5,738,474 A | 4/1998 | Blewett |
| 5,749,896 A | 5/1998 | Cook |
| 5,758,812 A | 6/1998 | Raffoni |
| 5,814,055 A | 9/1998 | Knodel et al. |
| 5,890,642 A | 4/1999 | Sato |
| 5,930,896 A | 5/1999 | La Prelle |
| 5,941,890 A | 8/1999 | Voegele et al. |
| 5,947,363 A | 9/1999 | Bolduc et al. |
| 5,947,999 A | 9/1999 | Groiso |
| 5,951,576 A | 9/1999 | Wakabayashi |
| 5,972,023 A | 10/1999 | Tanner et al. |
| 5,993,476 A | 11/1999 | Groiso |
| 6,001,110 A | 12/1999 | Adams |
| 6,083,242 A | 7/2000 | Cook |
| 6,306,150 B1 | 10/2001 | Levinson |
| 7,398,907 B2 | 7/2008 | Racenet et al. |
| 7,611,038 B2 | 11/2009 | Racenet et al. |
| 7,926,692 B2 | 4/2011 | Racenet et al. |
| 8,123,101 B2 | 2/2012 | Racenet et al. |
| 8,684,249 B2 * | 4/2014 | Racenet et al. ............ 227/176.1 |
| 2002/0029044 A1 | 3/2002 | Monassevitch et al. |

FOREIGN PATENT DOCUMENTS

| | | |
|---|---|---|
| EP | 0251444 A | 1/1988 |
| EP | 0517975 A | 12/1992 |
| EP | 0541950 A | 5/1993 |
| FR | 716780 | 12/1931 |
| FR | 2603794 | 9/1986 |
| GB | 1339394 A | 12/1973 |
| WO | WO 95/18572 A | 7/1995 |
| WO | WO 9518572 | 7/1995 |

OTHER PUBLICATIONS

International Search Report for PCT/US01/50721 date of completion is Oct. 21, 2002 (5 pages).

* cited by examiner

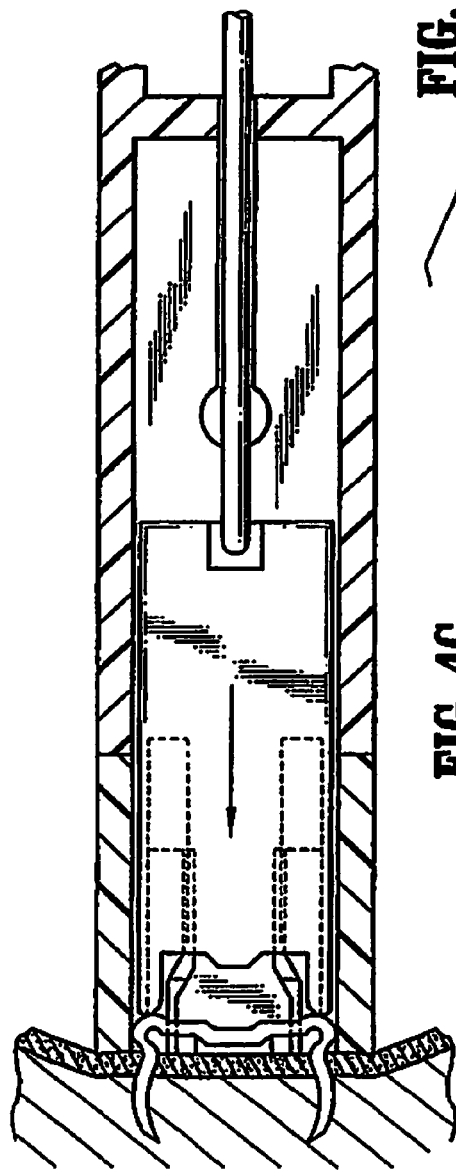
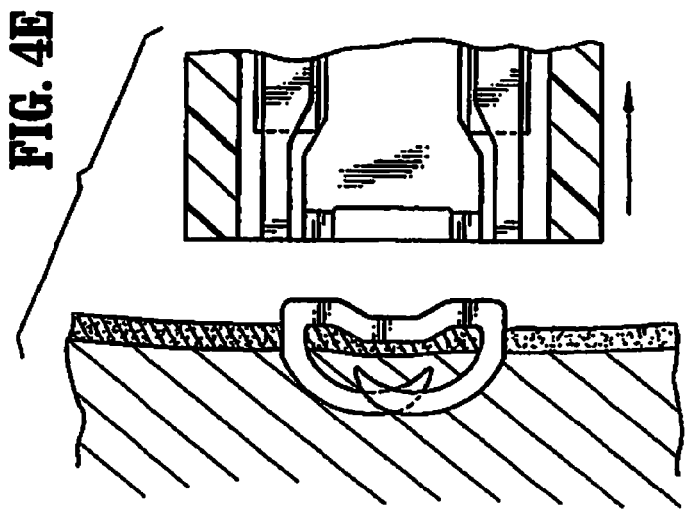
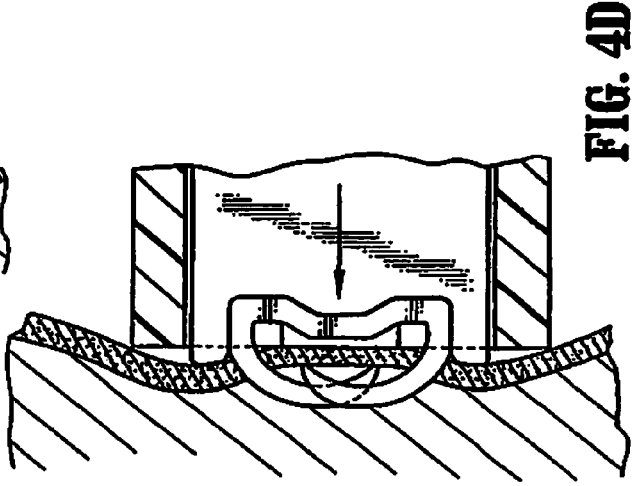
FIG. 4C
FIG. 4D
FIG. 4E

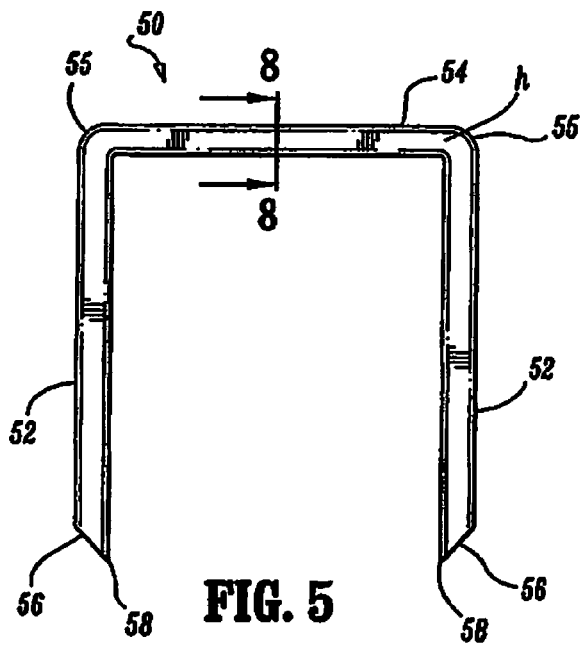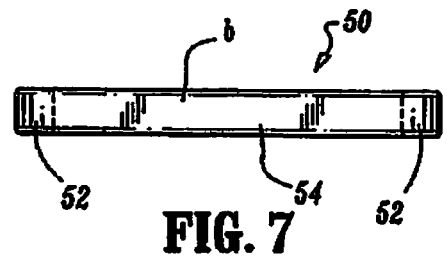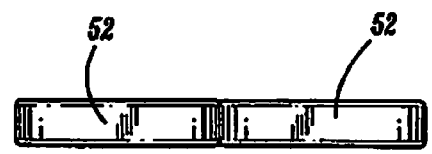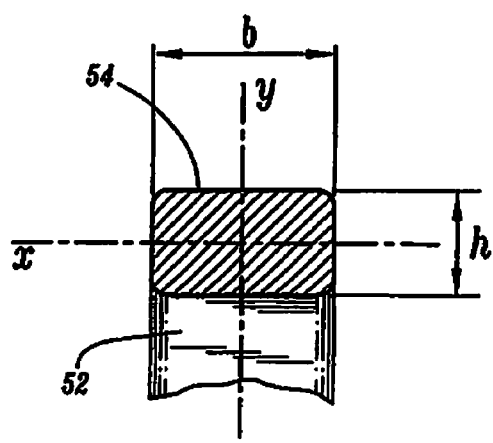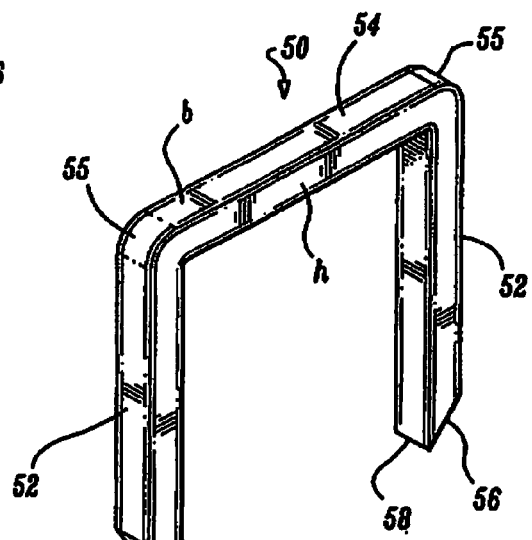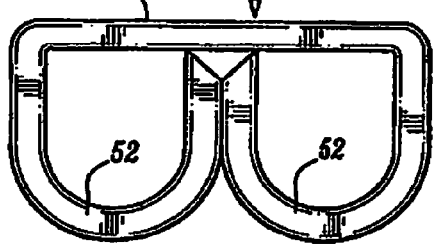

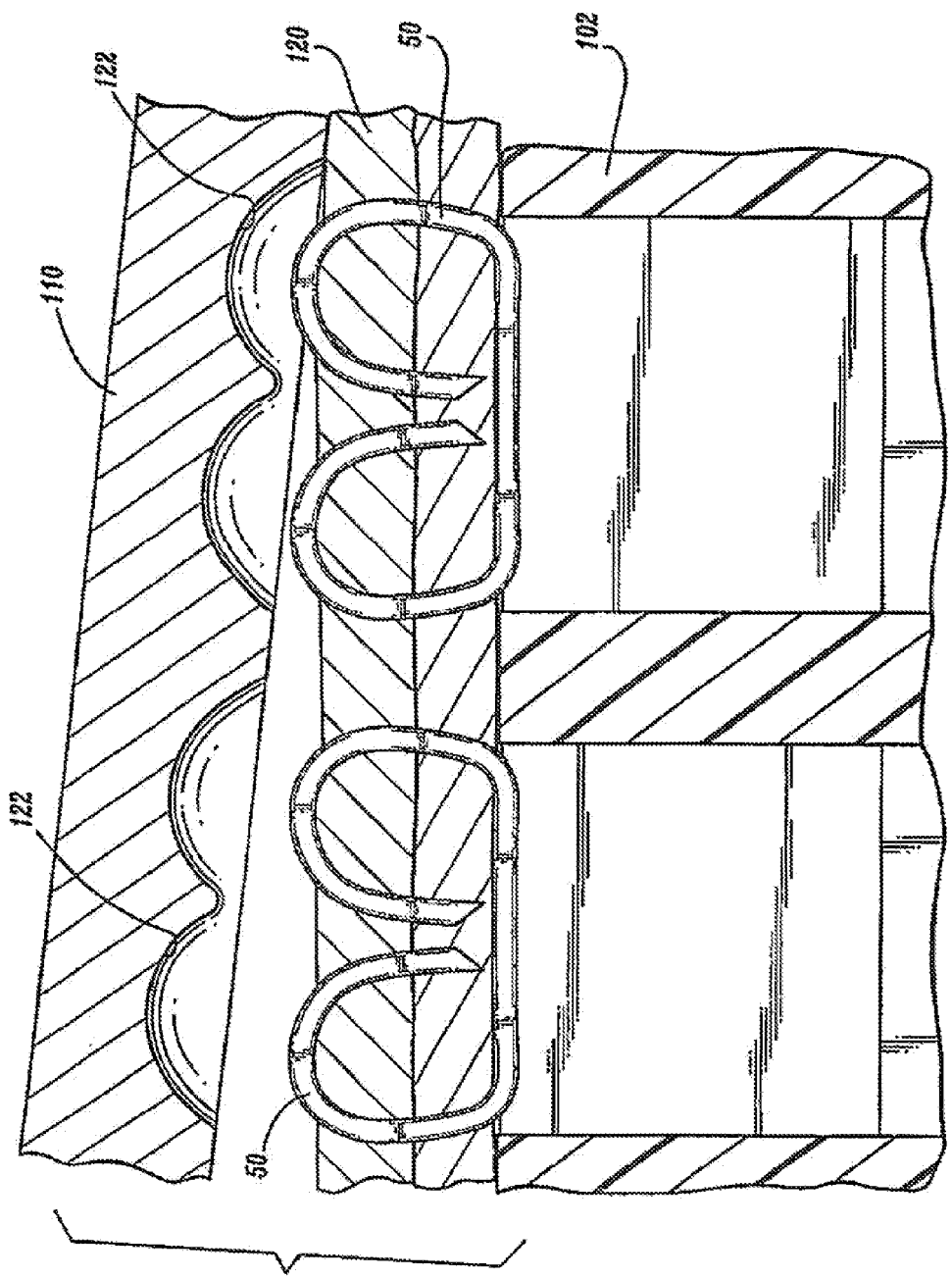

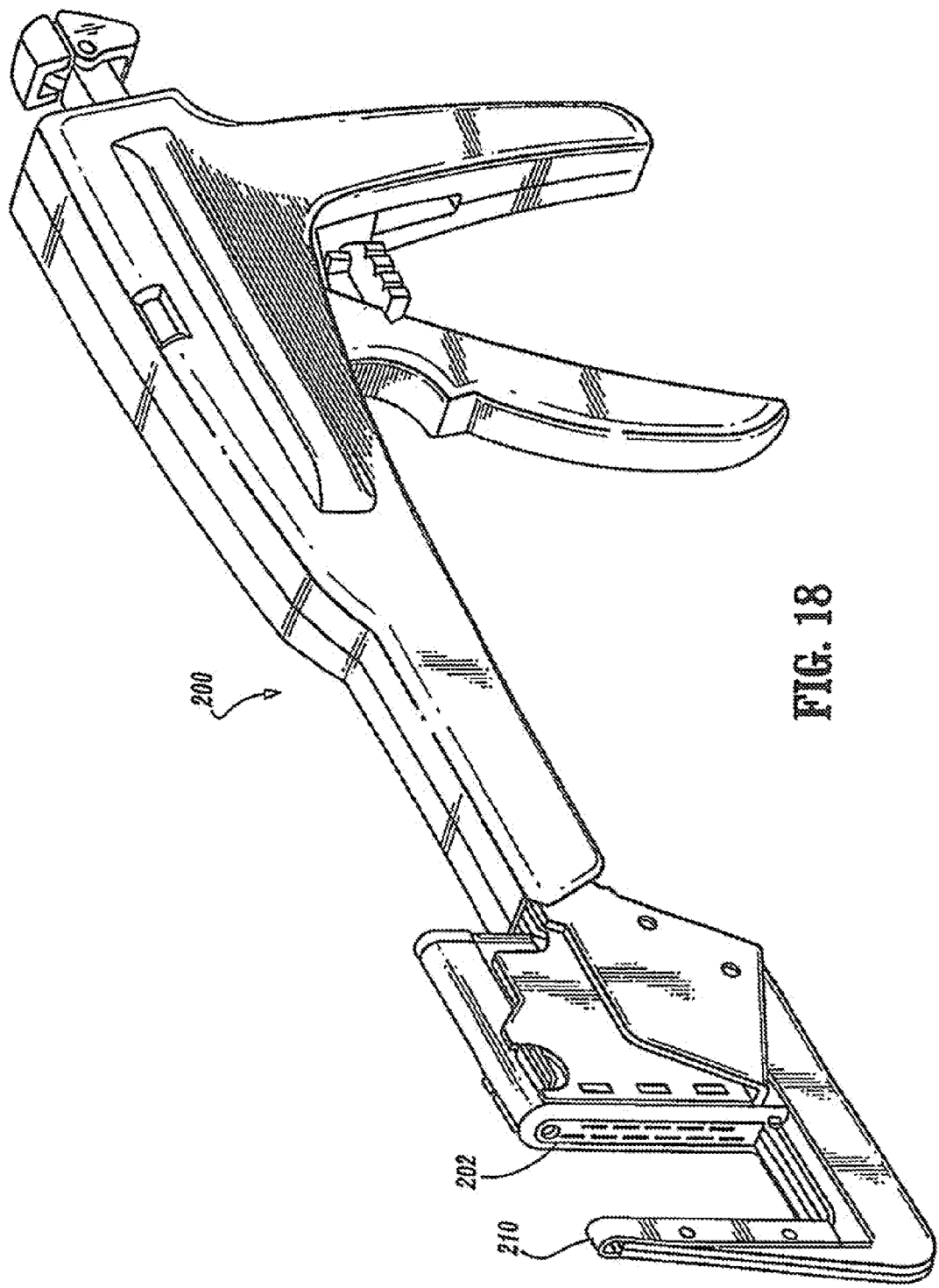

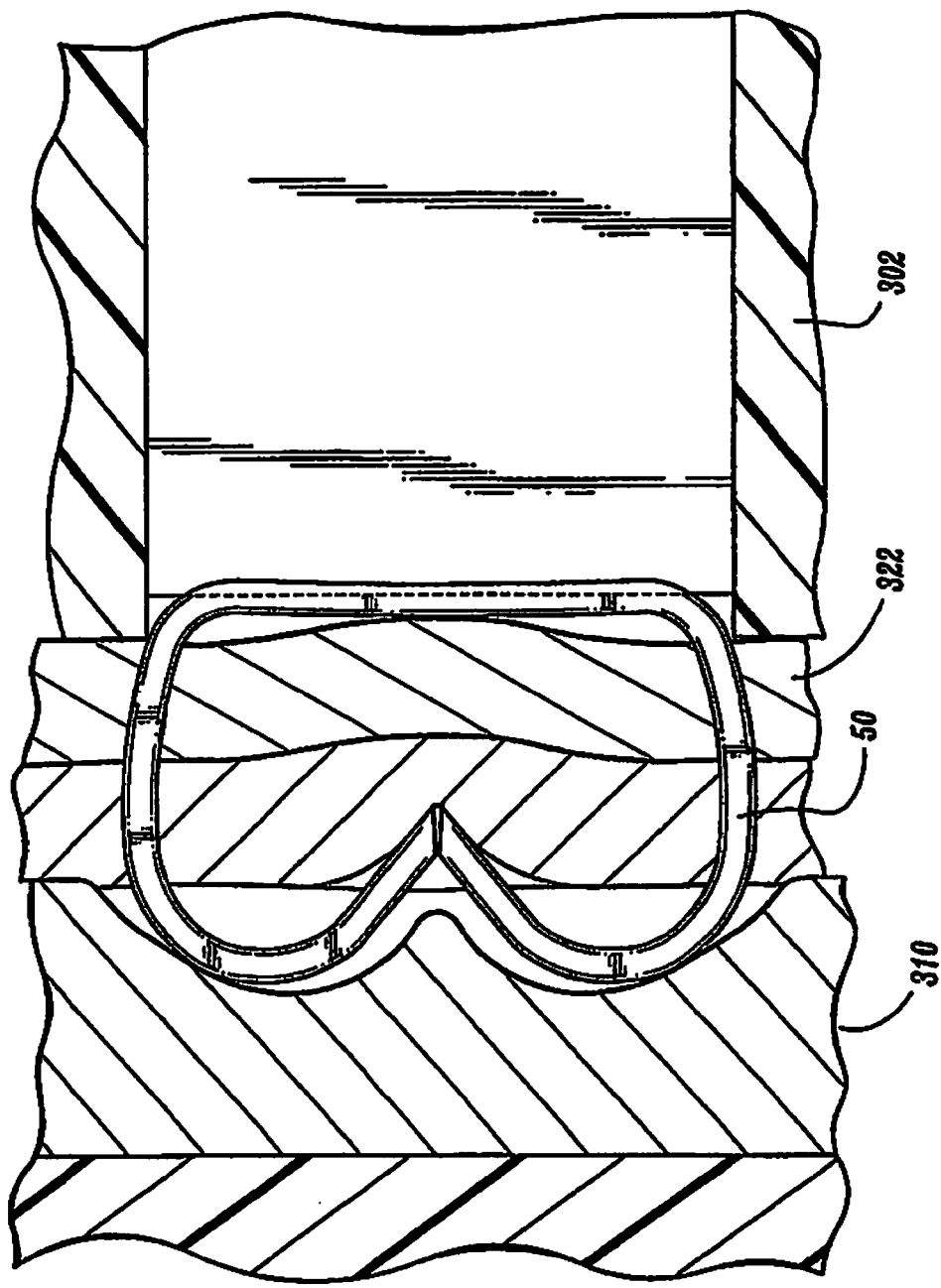

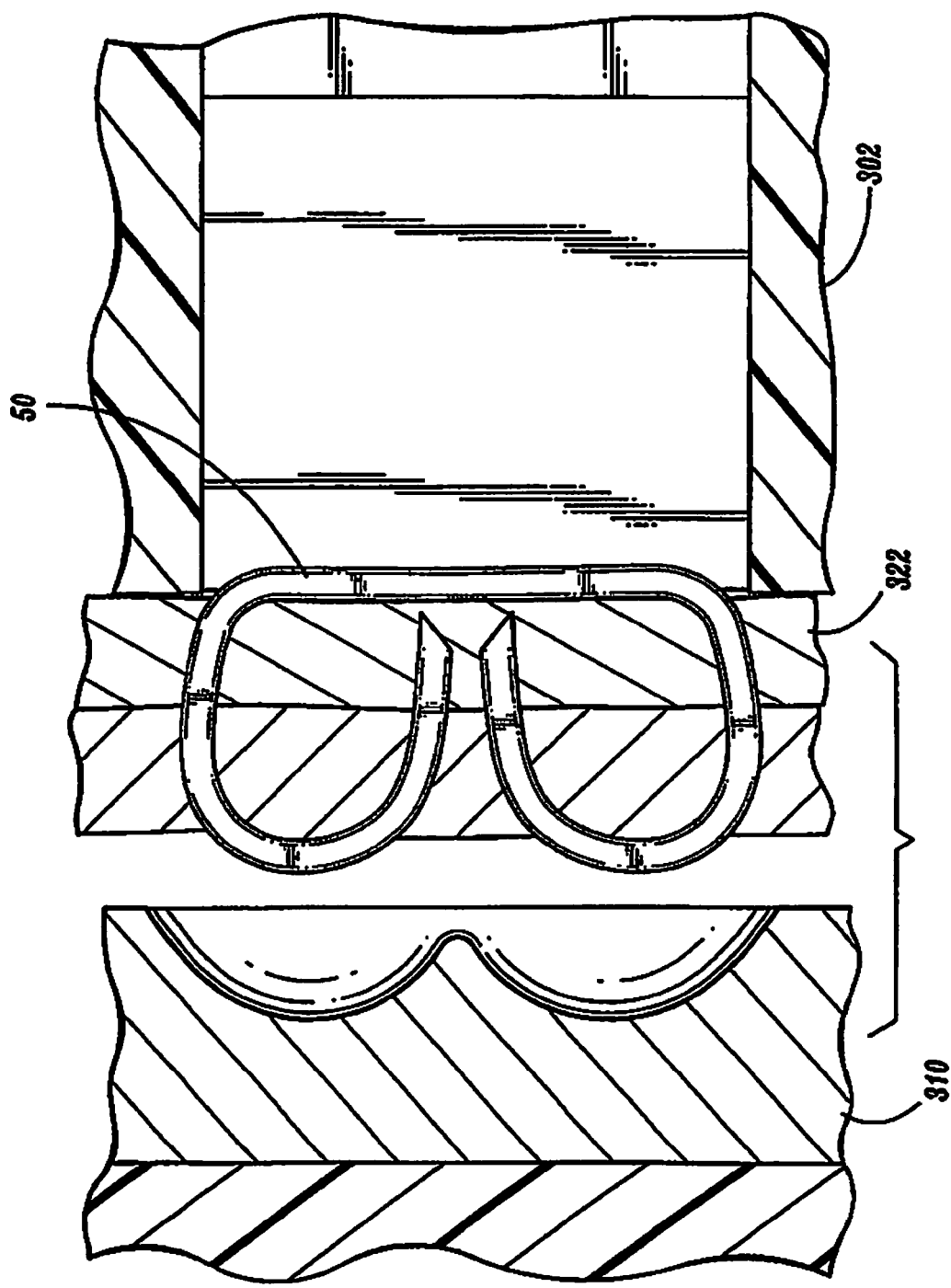

DIRECTIONALLY BIASED STAPLE AND ANVIL ASSEMBLY

CROSS-REFERENCE TO RELATED APPLICATIONS

This application is a continuation of and claims the benefits of and priority to U.S. patent application Ser. No. 13/368,407, which was filed on Feb. 8, 2012, now U.S. Pat. No. 8,684,249, which is a continuation of and claims the benefits of and priority to U.S. patent application Ser. No. 13/052,289, which was filed on Mar. 21, 2011, now U.S. Pat. No. 8,123,101, which is a continuation of U.S. patent application Ser. No. 12/568,135, which was filed on Sep. 28, 2009, now U.S. Pat. No. 7,926,692, which is a continuation of U.S. patent application Ser. No. 11/981,441, which was filed on Oct. 31, 2007, now U.S. Pat. No. 7,611,038, which is a continuation of U.S. patent application Ser. No. 11/253,493, which was filed on Oct. 17, 2005, now U.S. Pat. No. 7,398,907, which is a continuation of U.S. patent application Ser. No. 09/972,594, which was filed on Oct. 5, 2001 and which is currently abandoned, which is a continuation-in-part of U.S. patent application Ser. No. 09/693,379 which was filed on Oct. 20, 2000 and which is currently abandoned. The entire contents of each of these applications are incorporated herein by reference.

BACKGROUND

1. Technical Field

This invention relates to formable surgical fasteners and, more particularly, to directionally biased formable staples for use in surgical staplers having anvil pockets for forming the staples. This invention also relates to anvil assemblies including anvil pockets for use with surgical staplers.

2. Background of Related Art

Surgical stapling instruments have become critical to many life saving surgical procedures. Surgical staples are usually mechanically inserted into tissue with surgical stapling instruments such as those known as anastomosis devices, including gastrointestinal anastomosis devices and transverse anastomosis devices. In such devices, the staples are loaded in one or more elongated rows into a cartridge. A mechanism for pushing, or driving the stapler is actuated to drive the staples through two or more sections of tissue toward a deforming anvil. At the conclusion of the driving operation, the legs of each staple are conventionally clamped or bent, by the anvil, to a closed configuration to complete the suture and join the tissue sections together. Gastrointestinal anastomosis-type devices drive and bend the staples aligned in a row sequentially in rapid sequence, while transverse anastomosis-type devices drive and bend all staples simultaneously. See, e.g. U.S. Pat. Nos. 4,520,817 and 4,383,634. Circular anastomosis-type devices simultaneously apply annular rows of staples to tissue. See, e.g. U.S. Pat. No. 4,304,236.

One type of conventional staple 20, shown in FIGS. 1-3, used with both gastrointestinal anastomosis and transverse anastomosis-type surgical stapling devices is made of stainless steel or titanium. The undeformed staple 20 (FIG. 1) is generally U-shaped and includes a back span 22 and two legs 24 depending substantially perpendicularly from the back span. Each leg 24 has a sharp chiseled end point 26 for piercing body organs or tissue. The chisel point also creates torque in the staple, allowing it to form. The staple penetrates the tissue from one side to engage an anvil spaced apart and located at an opposing side of the tissue. The staple is bent by having the legs engage and follow an anvil 25 to form a B-shaped closed staple 28 as shown in FIG. 2. In this closed configuration tissue is compressed between the legs and backspan of the staple.

Because of their substantially circular cross-section (FIG. 3), these conventional staples require approximately the same amount of force to form the staple into its final shape as is required to twist or malform it.

For example, referring back to FIG. 3, a conventional round cross section staple has a moment of inertia in the x forming dimension ($I_x$) given by the equation:

$$I_x = \tfrac{1}{4}\pi r^4$$

Its moment of inertia in the y twisting dimension ($I_y$) is given by the same equation:

$$I_y = \tfrac{1}{4}\pi r^4$$

Using a round wire stock of uniform 0.009 in diameter (r=0.0045), $$I_x = I_y$$
$$= 1/4\pi(.0045)^4$$
$$= 3.22 \times 10^{-10} \text{in}^4$$

The Moment of Inertia Ratio, given by the equation: is $I_y/I_x$ $$\frac{3.22 \times 10^{-10} \text{in}^4}{3.22 \times 10^{-10} \text{in}^4} = 1$$

In order to insure accurate and consistent formation of these conventional staples, considerable research and development has been conducted in the areas of forming and driving structures. For example, anvils have been developed with specific coatings and/or structure, see, e.g. U.S. Pat. Nos. 5,173,133 and 5,480,089. Also, staple cartridges have been configured with driver structure to balance forces encountered during staple formation. See, commonly assigned U.S. Pat. No. 4,978,049 to Green. Thus, to control and insure consistent staple formation without twisting or deformation, extremely strict manufacturing tolerances have been implemented.

Other types of staples for different types of instruments are also found in the prior art. Some have non-circular cross-section. FIGS. 4, 4A and 4B illustrate by way of example a staple of this type marketed by United States Surgical of Norwalk, Conn. for use with its MULTIFIRE ENDO HERNIA and ENDO UNIVERSAL 65 staplers. The anvil in these staplers, as shown in FIGS. 4C and 4D, is adjacent the backspan of the staple as tissue is approached from only one side. Unlike the staples described above which are formed by contact of the staple legs with anvil pockets, these staple legs are bent around an anvil abutting the backspan. This staple has a side portion H with a height dimension greater than the dimension of the base portion B (i.e. 0.020 in vs. 0.015 in.).

The Moment of Inertia Ratio is given by the equation:

$$\text{Moment of Inertia Ratio} = \frac{I_y}{I_x}$$
$$= \frac{\text{Moment of Inertia About Twisting Axis}}{\text{Moment of Inertia About Forming Axis}}$$

where $I_x=(1/12)bh^3$ and $I_y=(1/12)hb^3$, with h=0.020 in. and b=0.015 in.
Thus, $I_x=(1/12)(0.015)(0.020)^3=1.0\times10^{-8}$ in$^4$, and $I_y=(1/12)(0.020)(0.015)^3=6.0\times10^{-9}$ in$^4$.
Accordingly, $$\text{Moment of Inertia Ratio} = \frac{6.01\times10^{-9}\text{in}^4}{1.10\times10^{-8}\text{in}^4}$$
$$= .60/1$$
$$= .60$$

This staple is specifically configured to accommodate twisting during staple formation to permit the legs of the staple to cross as shown in FIG. 4E. Thus, it is engineered so the force to form the staple is slightly greater than the force to malform or twist the staple. The forming is accomplished by bending the staple legs around an anvil positioned adjacent the inner surface 32 of the backspan 34.

U.S. Pat. No. 5,366,479 describes a hernia staple with adjacent anvil having a height of 0.38 mm and a thickness of 0.51 mm. This staple is formed the same way as in FIGS. 4C and 4D. The moment of inertia ratio of this staple in accordance with the foregoing formula is as follows:

$$I_x = (1/12)(.51)(.38)^3$$
$$= 2.33\times10^{-3}$$
$$I_y = (1/12)(.38)(.51)^3$$
$$= 4.2\times10^{-3}$$
$$\text{Moment of Inertia Ratio} = \frac{4.2\times10^{-3}}{2.33\times10^{-3}}$$
$$= 1.8$$

This staple for use as described would actually result in greater force to produce the desired shape. In fact, the staple legs would likely contact each other before crossing over into their crossed configuration.

Thus, it is apparent that this type of hernia staple, i.e. where the anvil is adjacent the backspan as the tissue is approached from only one side, is quite different than the staple of the present invention, e.g. the B-shaped staple, wherein the legs penetrate through the tissue to contact anvil pockets. These anvil pockets direct the staple legs to form the staple into a closed configuration. Thus staple configuration and considerations of twisting, bending and staple formation of these hernia staples are inapplicable to these considerations for anvil pocket directed staples, such as the B-shaped staples.

It would therefore be desirable to provide a staple configuration for a staple designed to penetrate tissue and contact an anvil pocket on the opposing side of tissue, which, in complement with conventional cartridge and anvil technology, enhances correct staple formation while reducing twisting/malformation caused by misalignment or unusual tissue while minimizing reliance on strict manufacturing tolerances. It would also be desirable to provide an anvil assembly which would minimize staple malformations by misalignment or twisting during formation of the staple.

SUMMARY

In accordance with the present disclosure a directionally biased staple is provided for use in surgical staplers having anvil structure spaced from the cartridge and having anvil pockets against which the staple is formed as the legs are forced into contact with the anvil. The directionally biased staple may be constructed in a wide variety of cross-sectional configurations including rectangular, elliptical, trapezoidal, etc. All of the configurations are distinguished by having a bending region requiring more force to twist or malform the staple than is required to properly form the staple. Preferably, these staples have Moment of Inertia Ratios on the order of between about 1.1 to about 3.0. The staple preferably corresponds in other respects to conventionally formed staples, i.e. having at least a pair of leg members interconnected by a crown portion wherein the leg members come into contact with and are formed by the anvil.

An anvil assembly is also provided which includes a tissue engaging surface and a plurality of staple pockets formed therein and configured to improve the formation of a staple during formation of the staple. Each staple pocket includes a pair of staple forming cups and a channeling surface positioned at least partially about each cup. Each cup includes an inside portion and an outside portion. The inside portion of each cup is positioned adjacent the inside portion of the other cup. Each cup includes a sidewall which defines an angle with respect to the tissue engaging surface which approaches perpendicular in a direction moving from the outside of the cup portion towards the inside portion of the cup. The sidewall defining at least the inside portion of each cup is substantially perpendicular to the tissue engaging surface of the anvil assembly such that each staple forming pocket defines a substantially vertical trap for minimizing misalignment and malformation of a staple.

BRIEF DESCRIPTION OF THE DRAWINGS

Various preferred embodiments are described herein with reference to the drawings, wherein:

FIGS. 4C, 4D and 4E illustrate the staple of FIG. 4 being formed as the legs are bent by the pusher and the backspan is held against the anvil;

FIG. 5 is a side view of a directionally biased staple in accordance with the present disclosure;

FIG. 6 is a perspective view of the staple of FIG. 5;

FIG. 7 is a top view of the staple of FIG. 5;

FIG. 8 is a cross-sectional view of the staple of FIG. 5 taken along line 8-8;

FIG. 9A is a side view of the staple of FIG. 5 after it has been deformed to a "B" configuration;

FIG. 9B is an end view showing the coplanarity of the AB@ sections of the staple of FIG. 9A;

FIG. 18 is a perspective view of a transverse anastomosis-type device for firing the staple of FIG. 5;

FIGS. 19B and 19C are enlarged views showing the staple formation by the anvil pockets of the instrument of FIG. 19A;

DETAILED DESCRIPTION OF PREFERRED EMBODIMENTS

Figure 1:
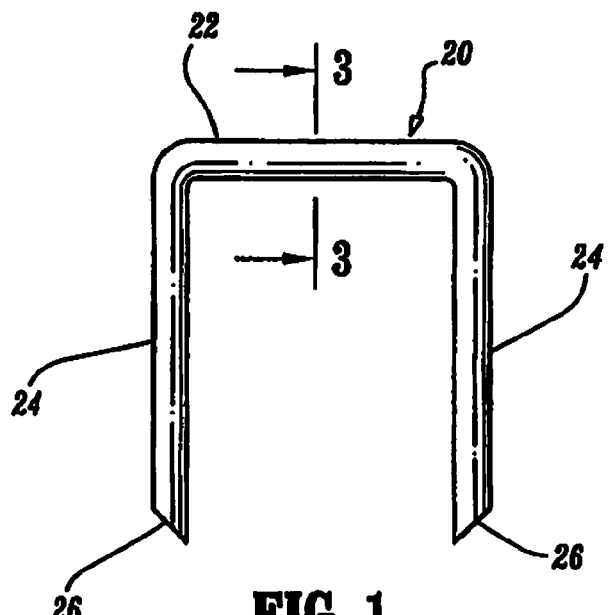
FIG. 1 is a side view of a conventional staple as known in the art.
Figure 2A:
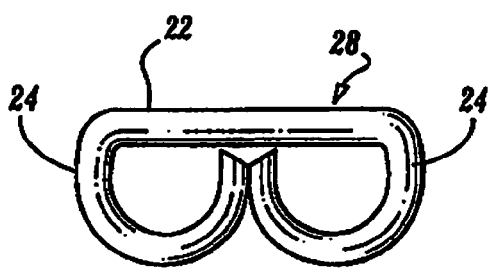
FIG. 2A is a side view of the staple of FIG. 1 formed into a "B" configuration.
Figure 3:
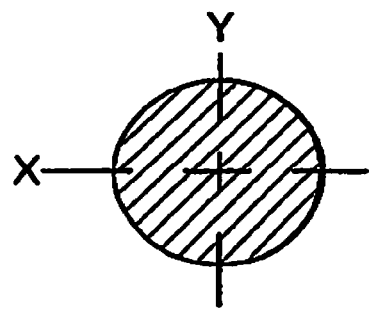
FIG. 3 is a cross-sectional view of the staple of FIG. 1 taken along line 3-3.
Figure 2B:
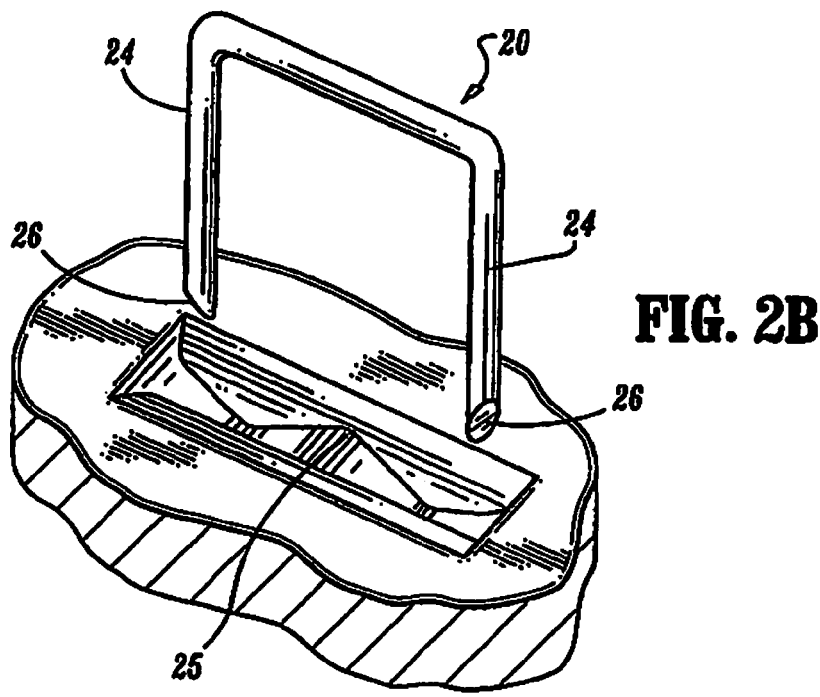
FIGS. 2B, 2C and 2D illustrate the staple of FIG. 2 being formed as the legs, after penetrating tissue, come into contact with the anvil pockets.
Figure 2C:
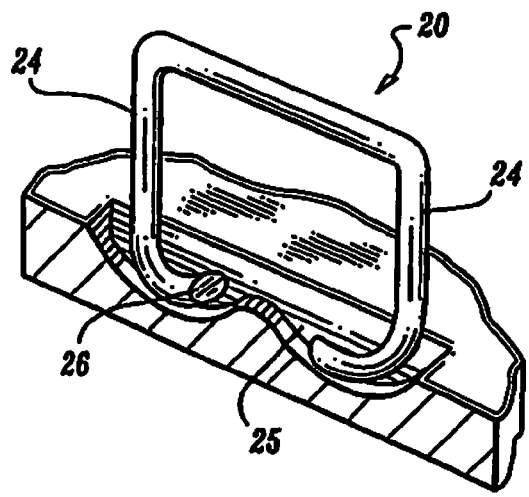
Figure 2D:
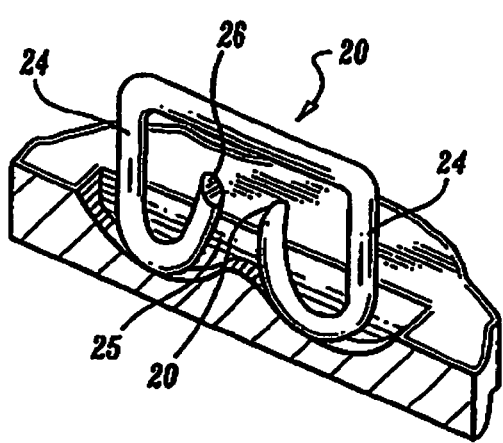
Figure 4:
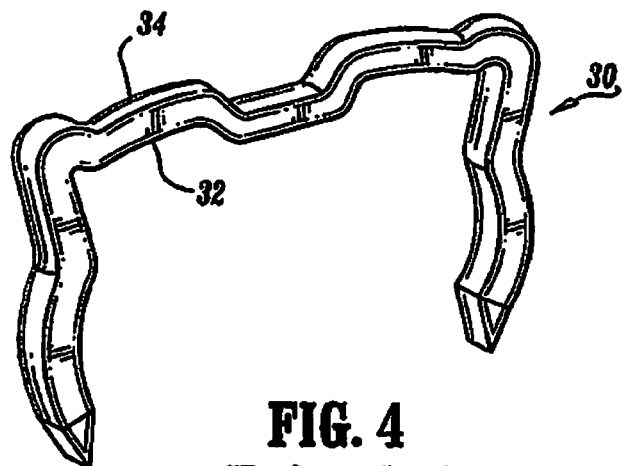
FIG. 4 is a perspective view of a conventional rectangular cross-section staple as known in the art which is formed around an anvil contacted by the backspan.
Figure 4A:
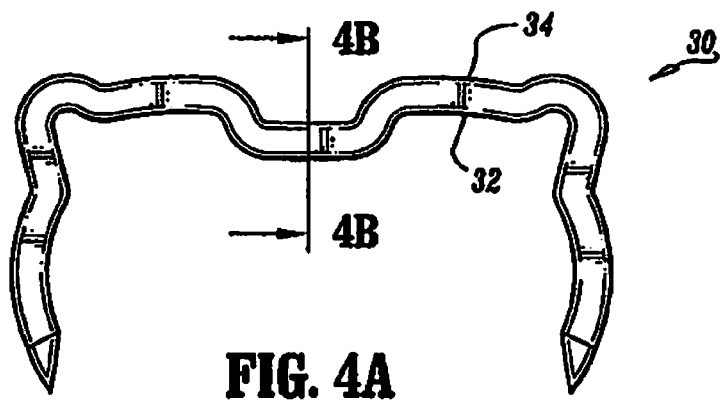
FIG. 4A is a side view of the staple of FIG. 4.
Figure 4B:
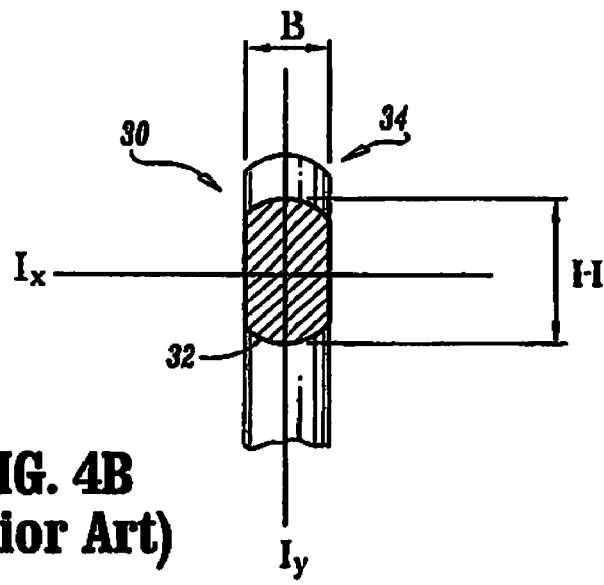
FIG. 4B is a cross-sectional view of the staple of FIG. 4 taken along line 4B-4B.
Figure 10A:
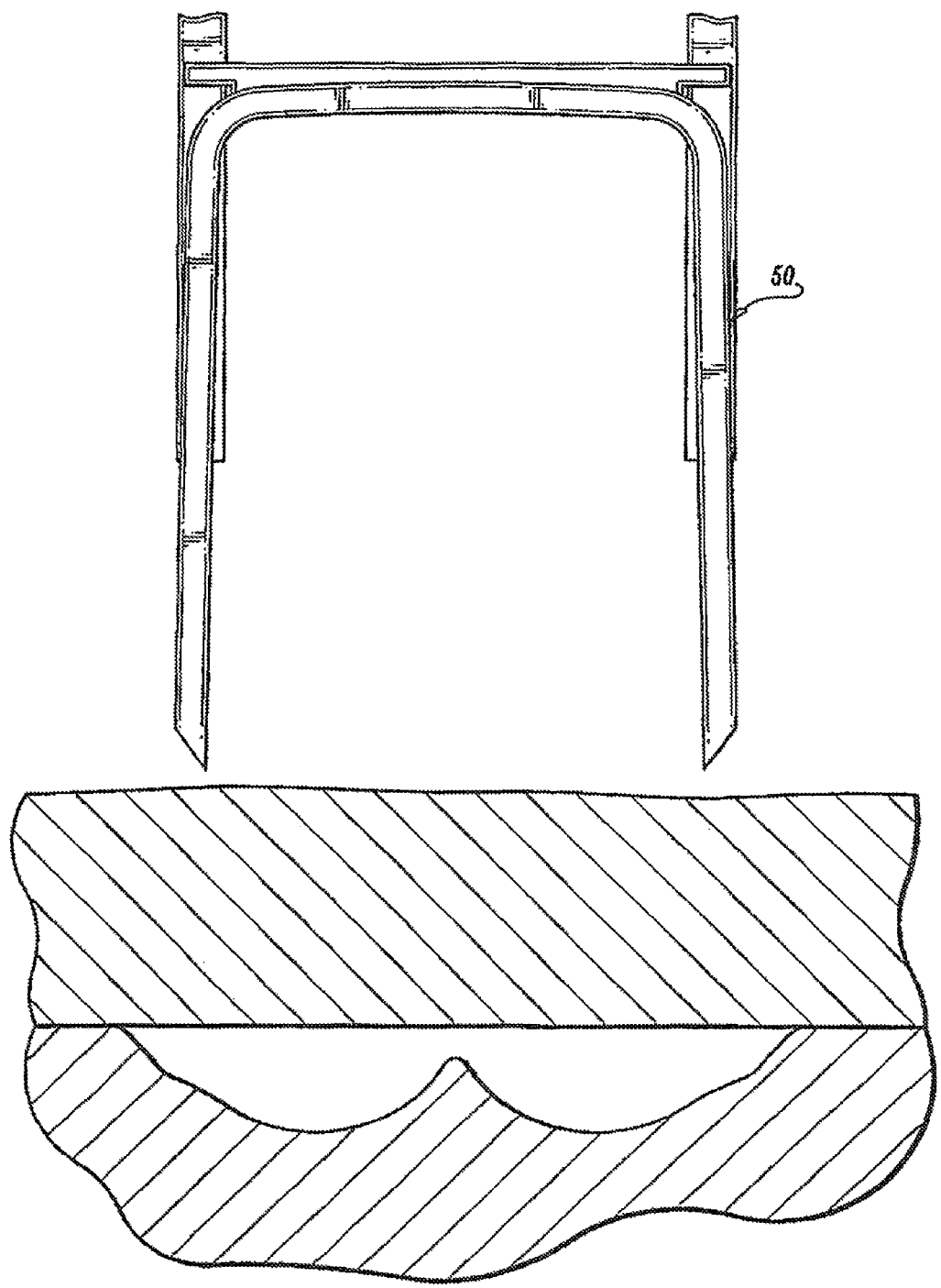
FIGS. 10A-10F are side views showing staple formation of the staple of FIG. 5 as the staple penetrates tissue and the legs come into contact with the anvil pockets.
Figure 10B:
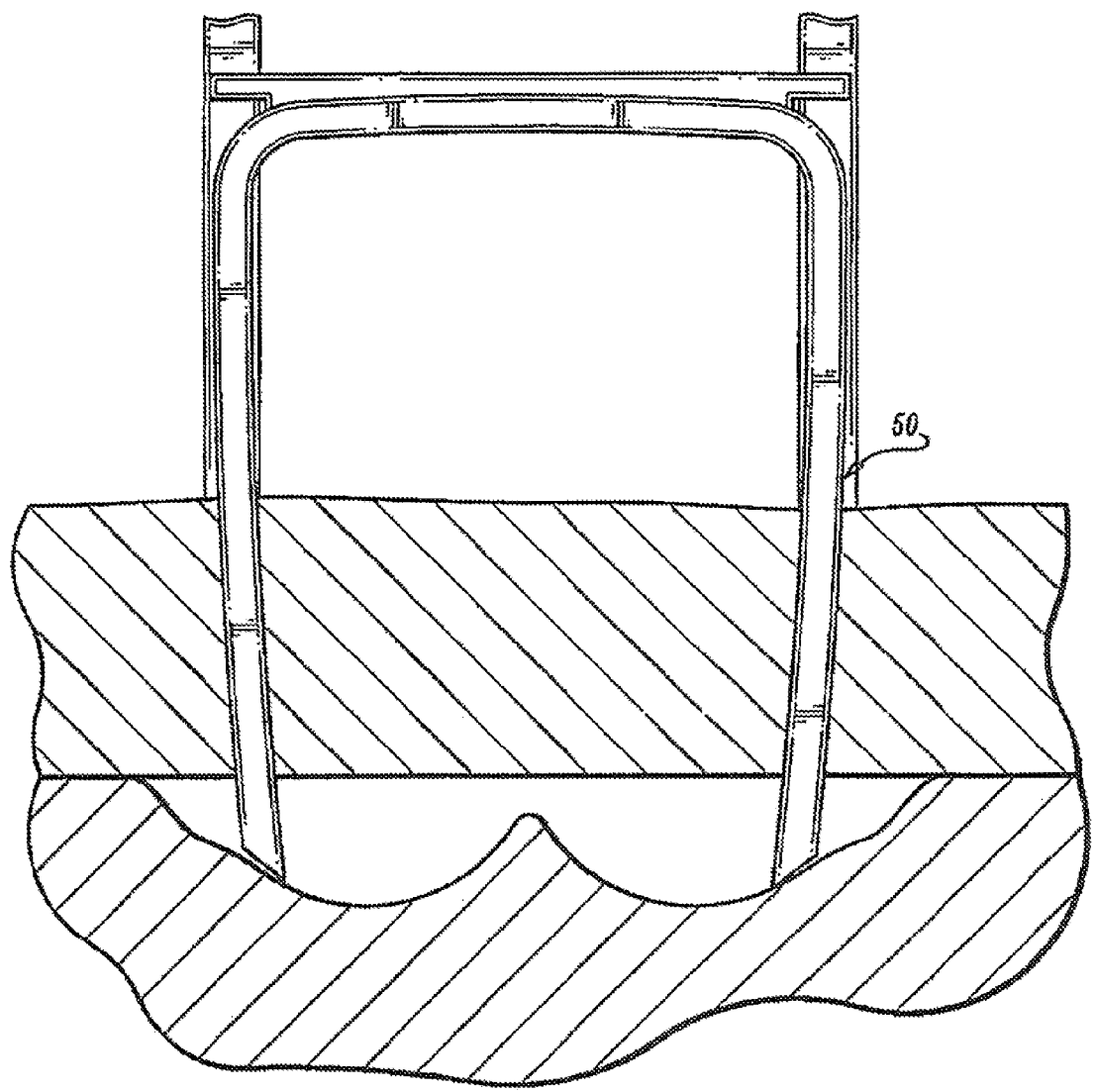
Figure 10C:
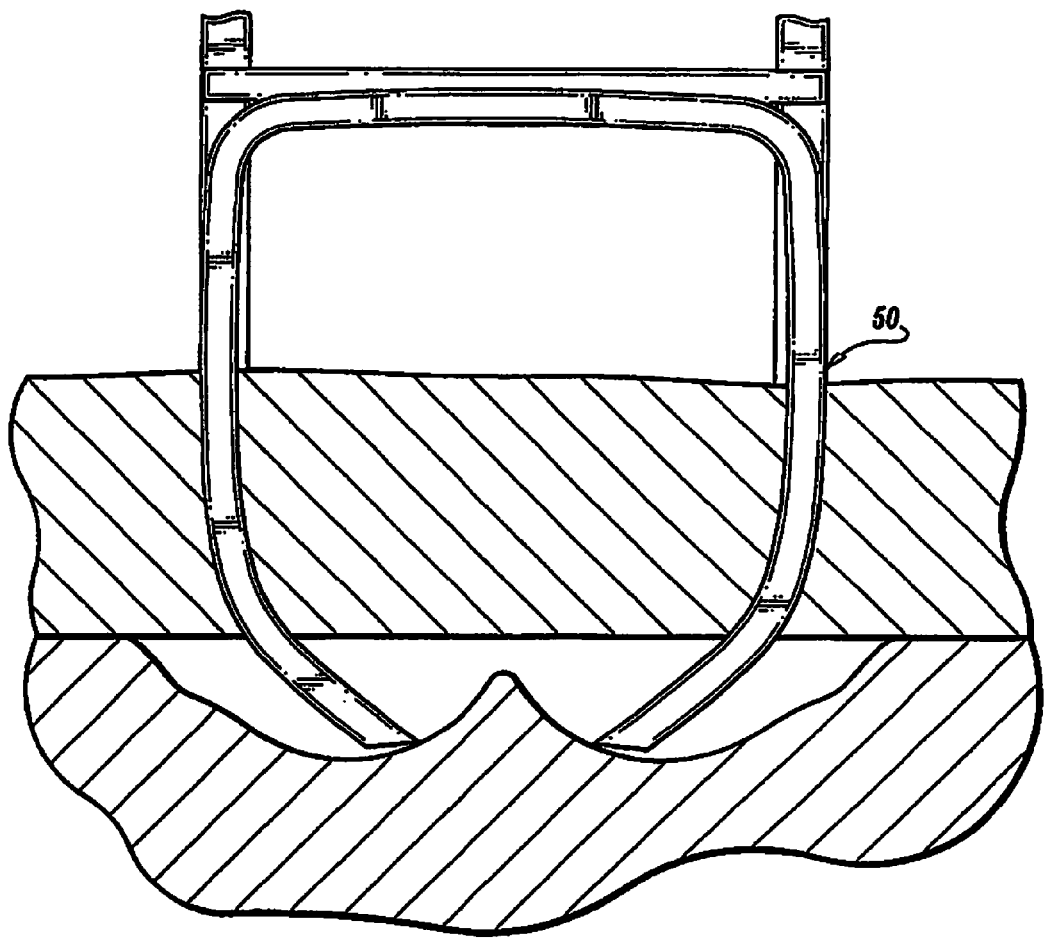
Figure 10D:
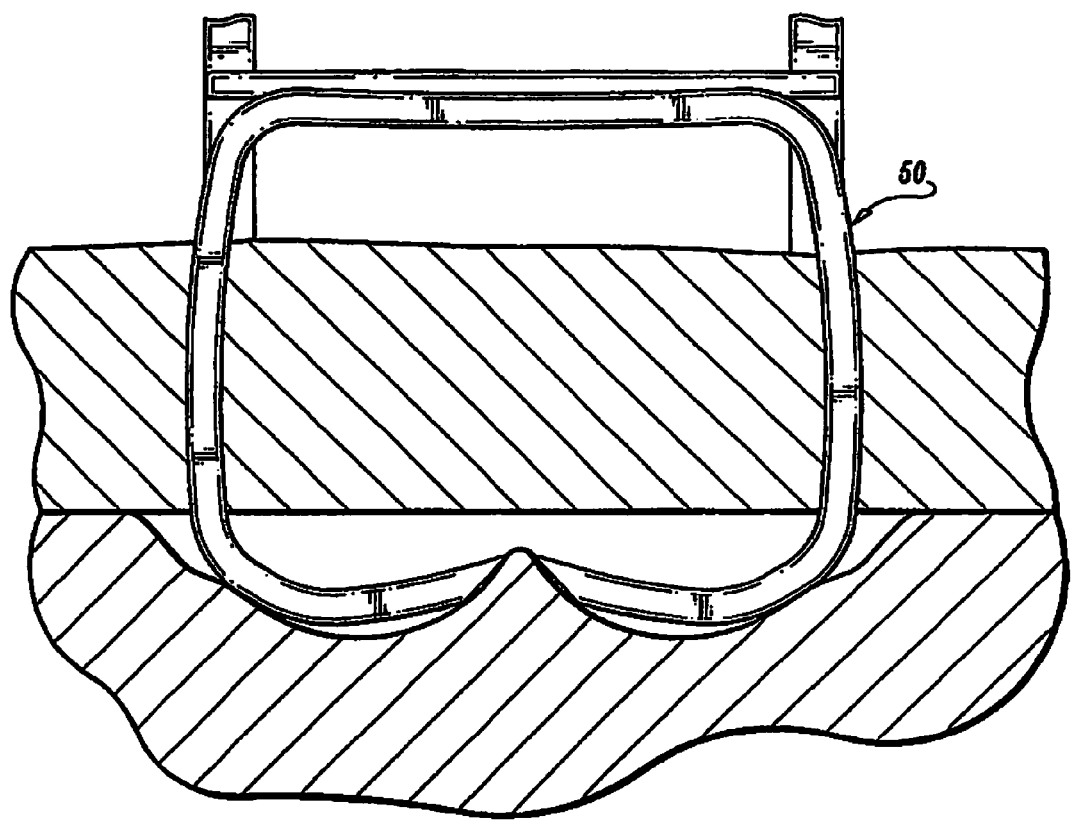
Figure 10E:
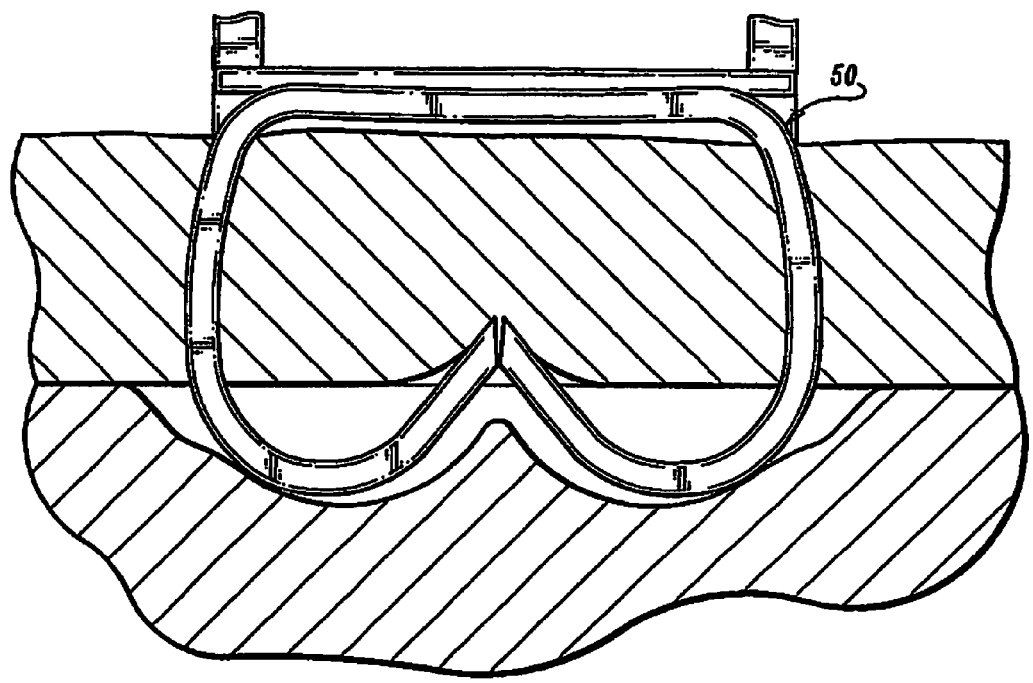
Figure 10F:
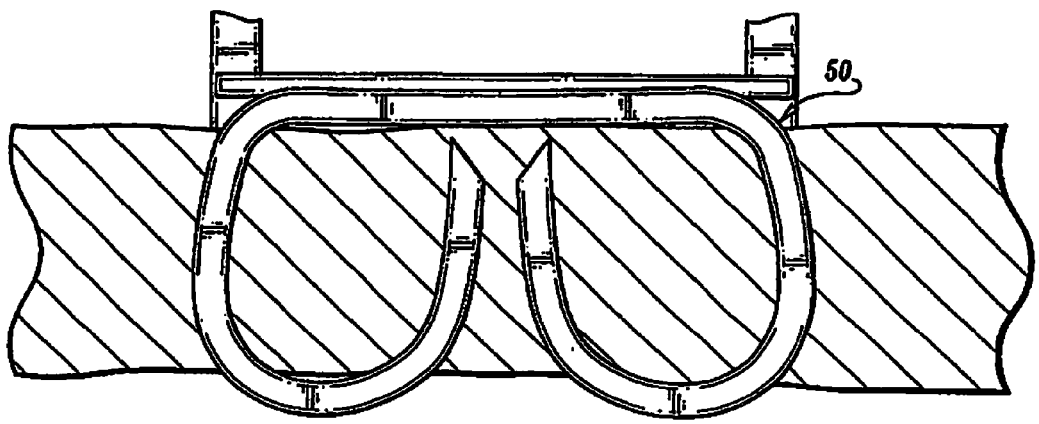

Preferred embodiments of the presently disclosed directionally biased staple will now be described in detail with reference to the drawings, in which like reference numerals designate identical or corresponding elements in each of the several views.

A directionally biased staple 50 in accordance with one embodiment of the present disclosure is illustrated in FIGS. 5-9. Referring specifically to FIGS. 5-7, staple 50 has a U-shaped configuration and includes a pair of substantially parallel legs 52 connected by a crown portion 54 with a bending region 55 therebetween. The legs are shown perpendicular to the backspan and are substantially straight along their length. Tissue penetrating portions 56 are preferably formed adjacent a distal end of legs 52. These penetrating portions 56 may be of any known configuration which facilitates entry of the legs 52 into tissue to be stapled. As shown in FIG. 5, the tissue penetrating portions 56 are preferably formed in a chisel shape with points 58 adjacent inner facing sides of legs 52.

In this embodiment, the cross section is preferably formed in a substantially rectangular configuration as shown in FIG. 8 with x designating the major base dimension (b) and y designating the minor height dimension (h) of the crown portion of the staple when positioned in an inverted-U configuration as shown in FIG. 5. As used herein, the staple is intended to be formed about the x dimension (x axis). Thus, as illustrated in FIGS. 10A-10F staple 50 is formed downward relative to the page.

This cross-sectional configuration may be achieved by any known method including extrusion, rolling, coining, etc. Preferably, this configuration is accomplished by flat rolling round wire stock on opposing sides. In the fabrication process, the stock can be pre-rolled by the wire manufacturer or may be round wire stock which is rolled into the desired cross-sectional configuration by the staple manufacturer.

$I_y$ of the cross-sectional configuration of the novel staple illustrated in FIG. 5 is given by the equation:

$$I_y = (1/12)(b)^3(h)$$

For a base dimension b=0.010 in and a height dimension h=0.008 in, $$I_y = (1/12)(0.010)^3(0.008)$$

$$I_y = 6.67 \times 10^{-10} \text{ in}^4$$

$I_x$ is given by the equation:

$$I_x = (1/12)(b)(h)^3$$

$$I_x = (1/12)(0.010)(0.008)^3$$

$$I_x = 4.26 \times 10^{-10} \text{ in}^4$$

The Moment of Inertia ratio ($I_y/I_x$) is thus $$\frac{6.67 \times 10^{-10} \text{in}^4}{4.26 \times 10^{-10} \text{in}^4} = 1.57$$

Similarly, for a base dimension b=0.012 in and a height dimension h=0.008 in, $I_x=1.0 \times 10^{-9}$ in$^4$ and $I_y=5.12 \times 10^{-10}$ in$^4$, yielding a Moment of Inertia ratio of 1.95.

Given that $I_y$ defines the dimension corresponding to proper formation of the staple when fired and $I_x$ defines the dimension corresponding to twisting and/or malformation, it is readily apparent that the directionally biased configurations provide a "functionally similar" forming force as a conventional round staple while requiring up to twice as much force to twist or malform when compared to conventional staples. This novel staple provides a substantial improvement over conventional staples.

Table 1 below sets forth by way of example Moment of Inertia Ratios for a variety of sizes and types of novel directionally biased staples for use in surgical staplers. Clearly staples of other dimensions are contemplated so long as they have the novel moment of inertia ratio described herein.

| Staple Size | Height (in.) | Base (in.) | $I_y$ | $I_x$ | $I_y/I_x$ Moment of Inertia Ratio |
|---|---|---|---|---|---|
| 3.5 mm. Titanim | .007 | .010 | $5.83 \times 10^{-10}$ | $2.86 \times 10^{-10}$ | _2.04/1 |
| 3.5 mm. StainlessSteel | .007 | .0115 | $8.87 \times 10^{-10}$ | $3.29 \times 10^{-10}$ | _2.70/1 |
| 3.8 mm. StainlessSteel | .007 | .010 | $5.83 \times 10^{-10}$ | $2.86 \times 10^{-10}$ | _2.04/1 |
| 4.8 mm. Titanim | .009 | .014 | $2.00 \times 10^{-9}$ | $8.51 \times 10^{-10}$ | _2.35/1 |
| 4.8 mm. Titanim | .007 | .0115 | $8.87 \times 10^{-10}$ | $3.29 \times 10^{-10}$ | _2.70/1 |

Further, as illustrated below, for comparable size staples, the novel staple configuration provides increased resistance to twist without changing firing forces.

For example, twisting stress _b is defined by the equation:

$$\_b = \frac{Mc}{Iy}$$

with moment M kept constant at M=1 lb$ in.

For a conventional round 0.009 in. diameter staple: M=1 lb$in; c=0.0045 in; and $I_x=I_y=3.22 \times 10^{-10}$ in$^4$, so $$\_b = \frac{(1.0 \text{ lb in})(.0045 \text{ in})}{3.22 \times 10^{-10} \text{in}^4}$$

$$\_b = 13,975 \text{ ksi}$$

For the directionally biased staple of FIG. 8 having b=0.010 in and h=0.008 in: M=1.0 lb$in; c=0.005 in; and $I_y=6.67 \times 10^{-10}$ in$^4$.

$$\_b = \frac{(1.0 \text{ lb in})(.005 \text{ in})}{6.67 \times 10^{-10} \text{in}^4}$$

$$\_b = 7,496 \text{ ksi}$$

Thus, not only is this embodiment of the novel staple more resistant to twisting and/or malformation, e.g. _14,000 ksi for the conventional staple vs. _7,500 ksi for the novel staple, it also maintains minimal firing forces. The directionally biased staple is effectively desensitized against the effects of misalignment during staple formation while, at the same time maintaining a minimal firing force. This directionally intelligent design can reduce malformations caused by misalignment or twisting as well as reduce the need for very sensitive manufacturing tolerances for anvils and anvil forming cups, cartridges, etc.

Figure 11A:
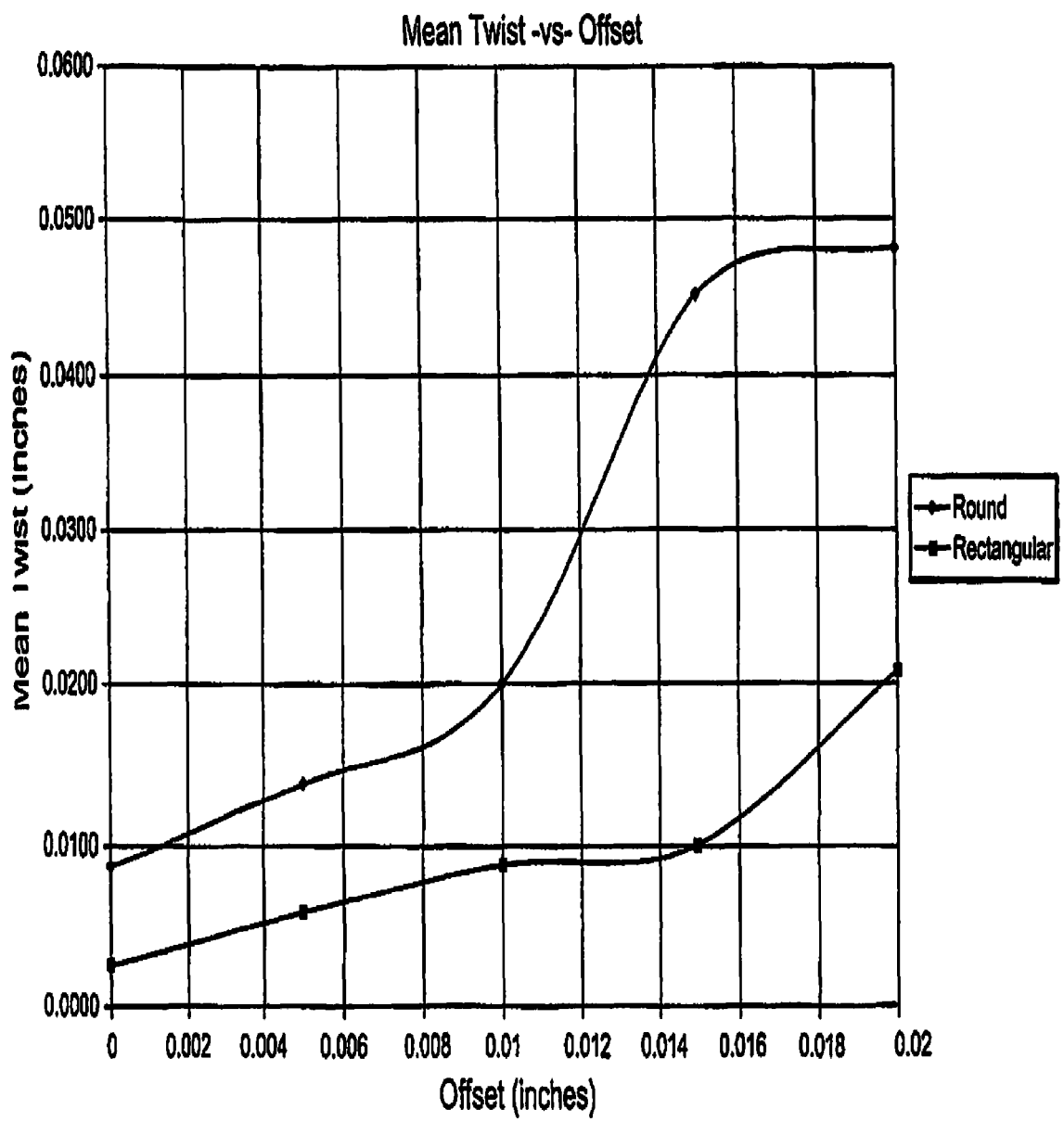
FIG. 11A graphically illustrates the comparison of the mean twist (in inches) vs the offset of the conventional staple of FIG. 1 and the novel staple of FIG. 5.
Figure 11B:
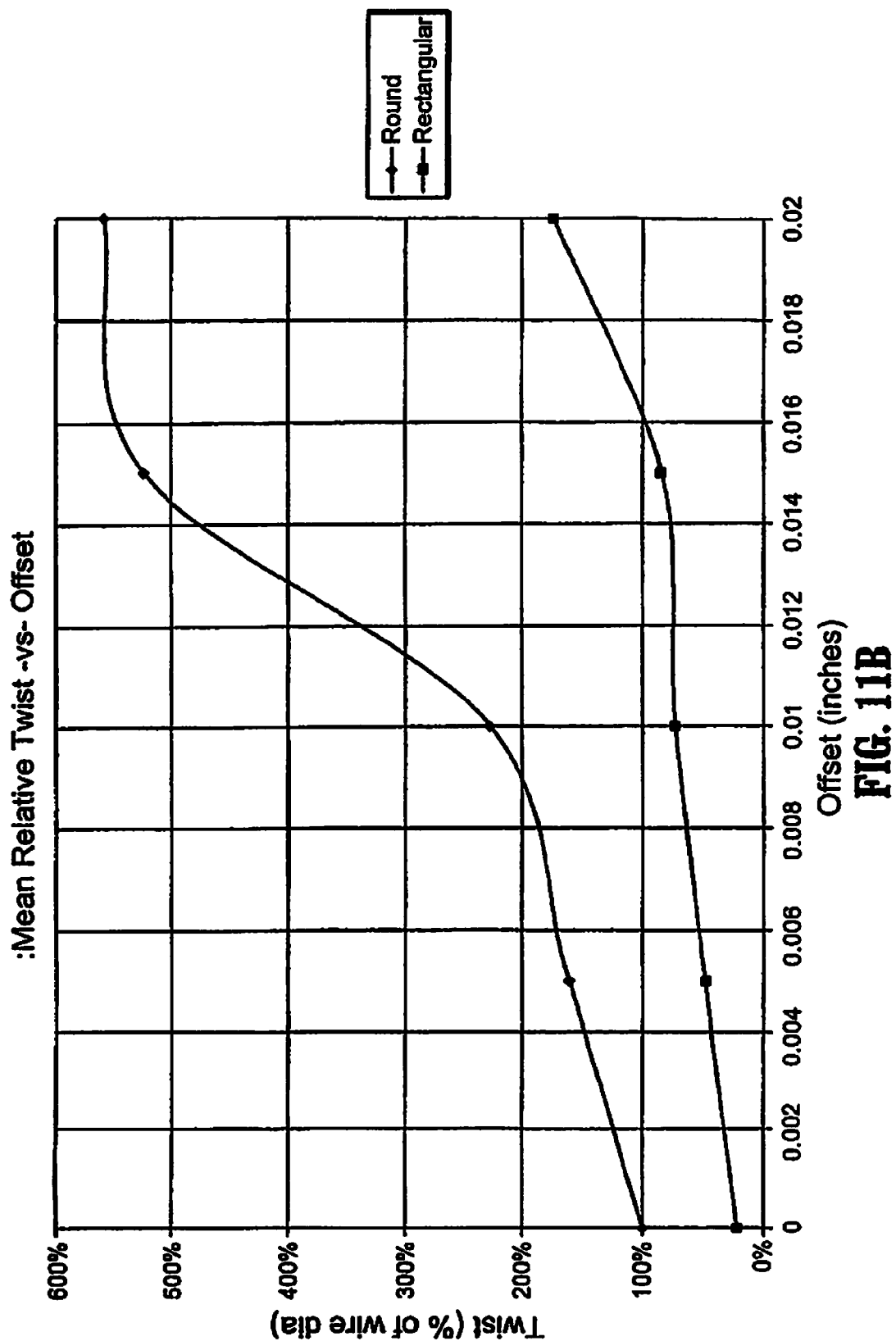
FIG. 11B graphically illustrates the comparison of the mean twist (in %) vs the offset of the conventional staple of FIG. 1 and the novel staple of FIG. 5.

The benefits of the novel staple can also be appreciated by reference to the graphs of FIGS. 11A and 11B. Since staples are forced through thick tissue and the staple cartridge and anvil can flex as tissue is compressed and can move slightly relative to another, this affects the point of contact between the staple leg points and the anvil. For example, if the anvil moves slightly out of alignment, the staple legs will contact a different point of the anvil which can affect uniform formation of the staple. Additionally, due to manufacturing tolerances, the staple points may not contact the anvil in the exact optimal location. Although such staple formation is clinically satisfactory and effective, the novel staple of the present application provides for more uniform formation of the row of staples and accommodates for manufacturing tolerances as it is more resistant to twisting. That is, the staple will have the tendency to bend in the direction of the thinner dimension which is desired since in this case the thinner dimension defines the desired bending direction. By relaxing manufacturing tolerances, the cost of manufacturing is reduced as well.

As shown in FIG. 11A, the prior art round staple, since the height and width are the same, can twist in different directions if there is misalignment between the staple and anvil. Thus the direction of twisting cannot be controlled. In contrast, the Moment of Inertia ratio of the novel staple of the present invention results in reduced twisting. Note that not only is there more twisting initially with the prior art staple, but as the offset increases, the amount of twisting in the current staple is greater at any degree of offset. The percentage of twist is defined as x/d×100% wherein x is the distance between the centerline of the staple and d is the diameter (or width) of the staple.

Figure 12A:
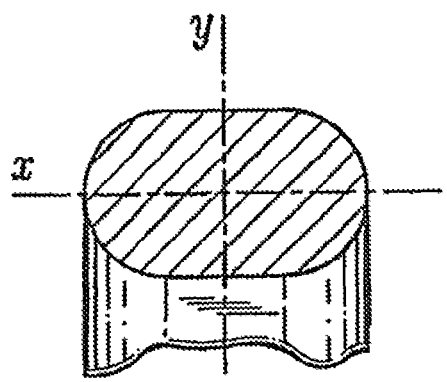
FIG. 12A is a cross-sectional view of another embodiment of a directionally biased staple in accordance with the present disclosure.
Figure 12C:
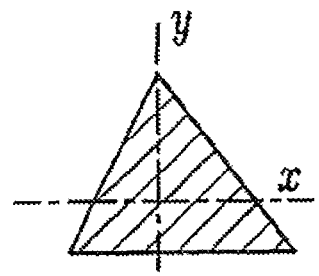
FIG. 12C is a cross-sectional view of another embodiment of a directionally biased staple in accordance with the present disclosure.
Figure 12B:
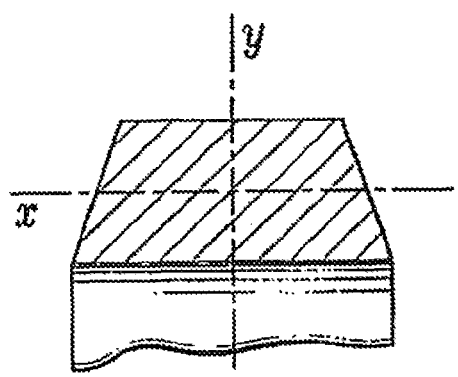
FIG. 12B is a cross-sectional view of another embodiment of a directionally biased staple in accordance with the present disclosure.
Figure 13:
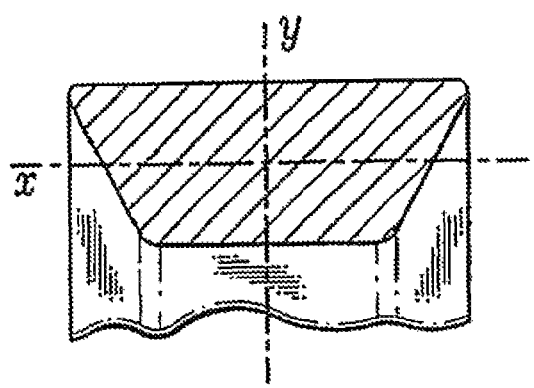
FIG. 13 is a cross-sectional view of another embodiment of a directionally biased staple in accordance with the present disclosure.
Figure 14:
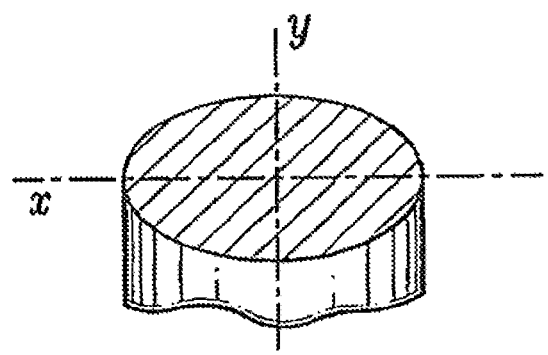
FIG. 14 is a cross-sectional view of another embodiment of a directionally biased staple in accordance with the present disclosure.

FIGS. 12-14 illustrate alternate directionally biased cross-sectional configurations in accordance with the disclosure. These cross-sectional configurations all have aspect ratios in the range of about 1.1 to about 3.0 wherein the x axis designates the major base dimension (b) and the y-axis designates the minor height dimension (h) in each of these cross-sections.

FIGS. 15-19 disclose by way of example several types of surgical staplers which can utilize the novel directionally biased staples. Other types of surgical staplers are also contemplated.

Figure 15:
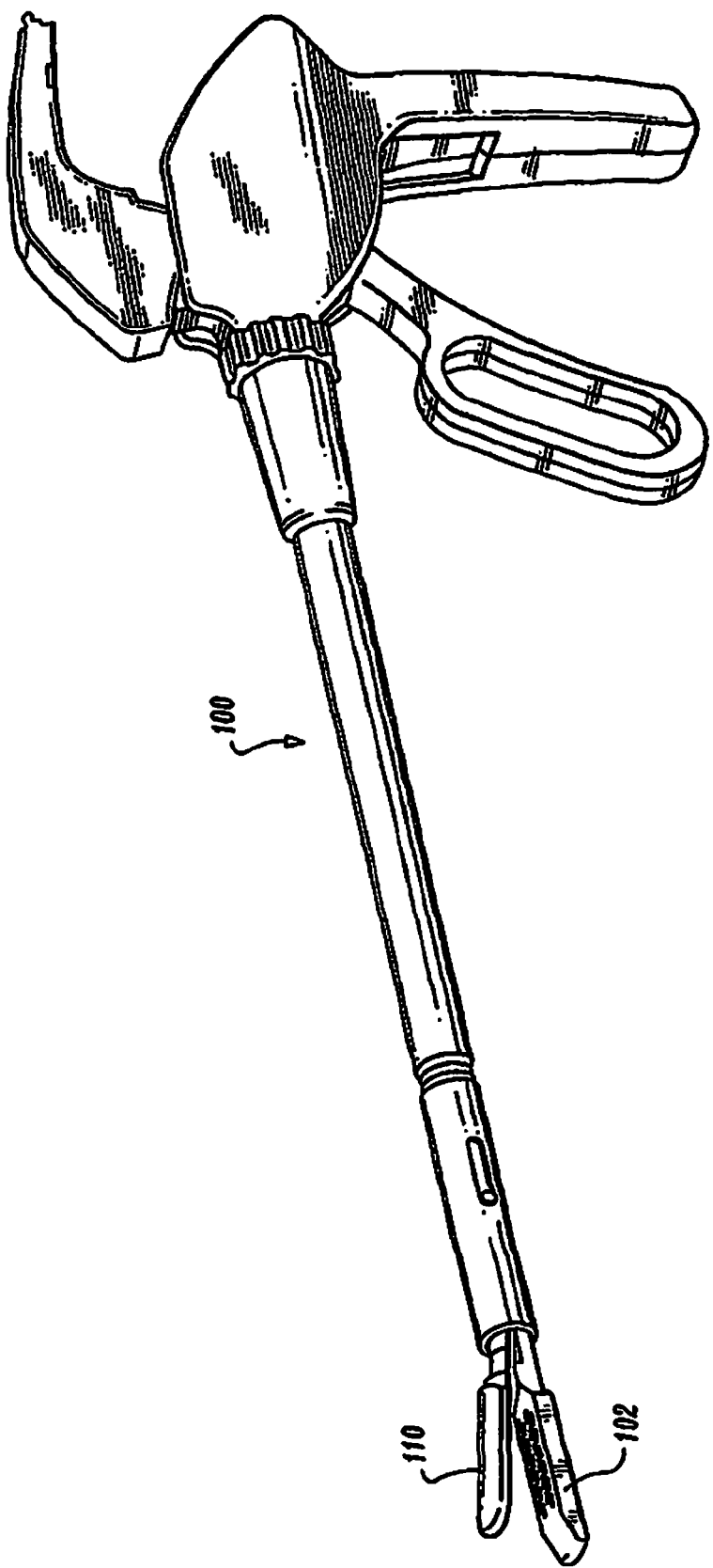
FIG. 15 is a perspective view of an endoscopic gastrointestinal anastomosis-type device for firing the staple of FIG. 5.
Figure 16:
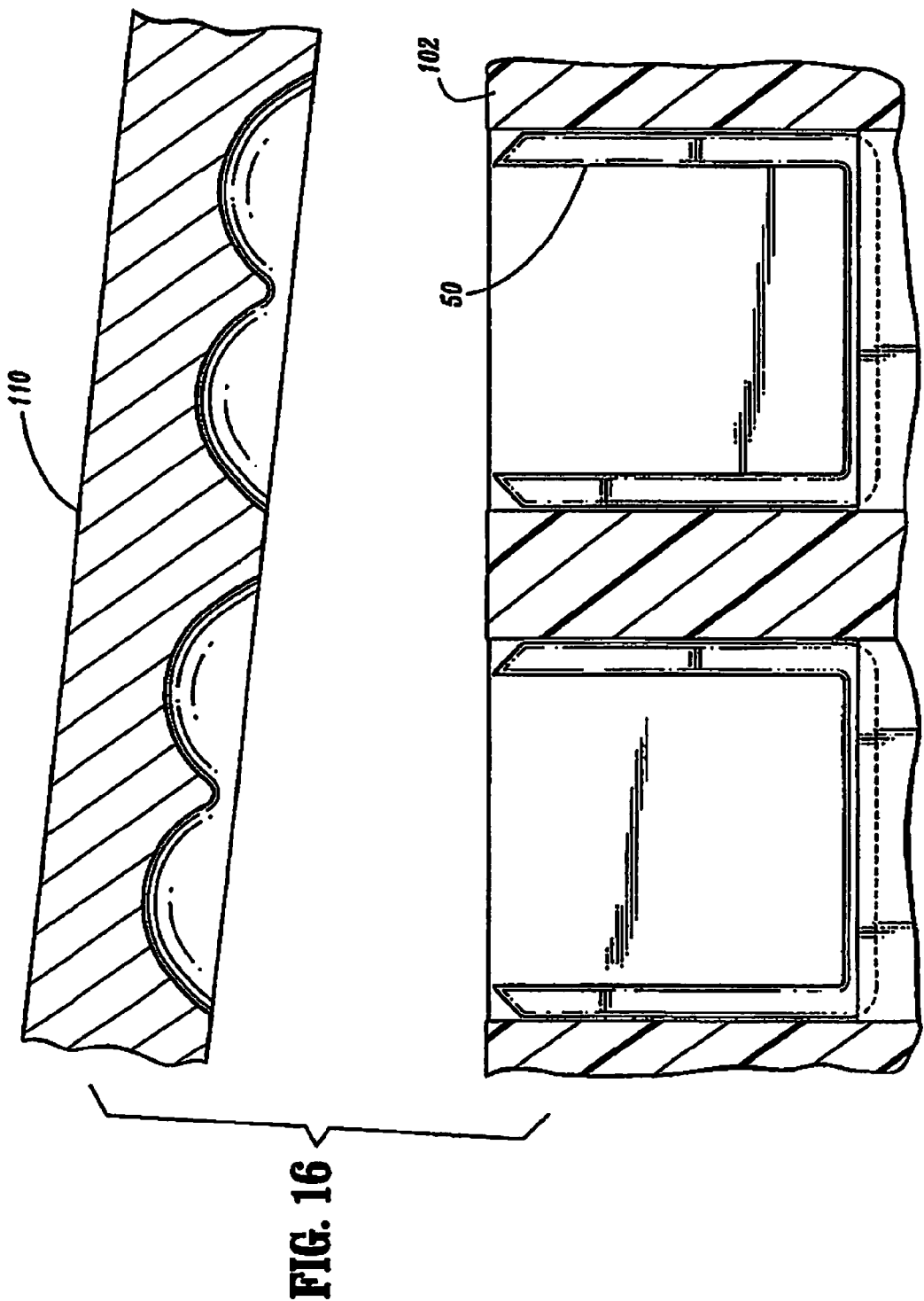
FIGS. 16-16C are enlarged views showing the staple formation by the anvil pockets of the instrument of FIG. 15.
Figure 16A:
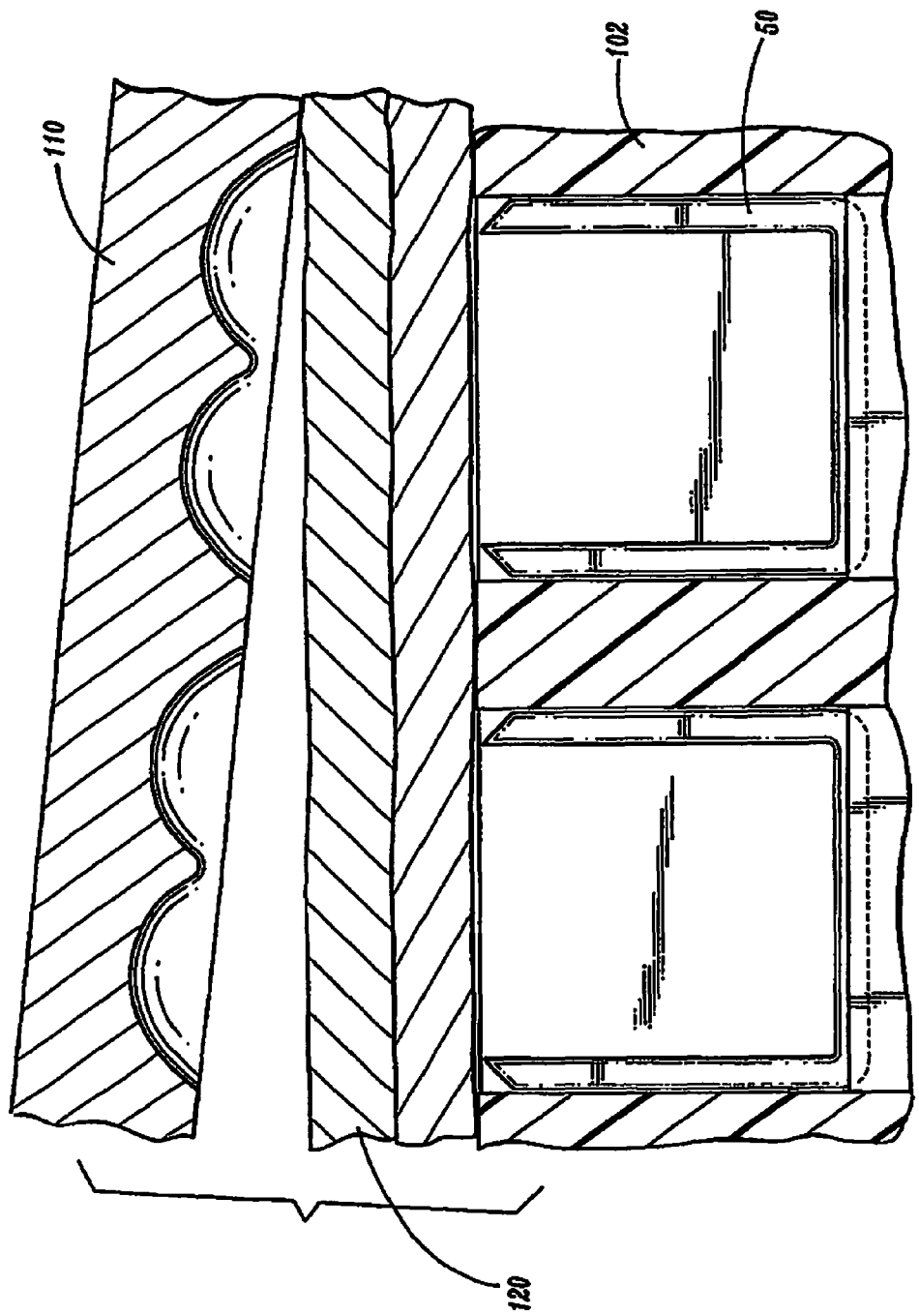
Figure 16B:
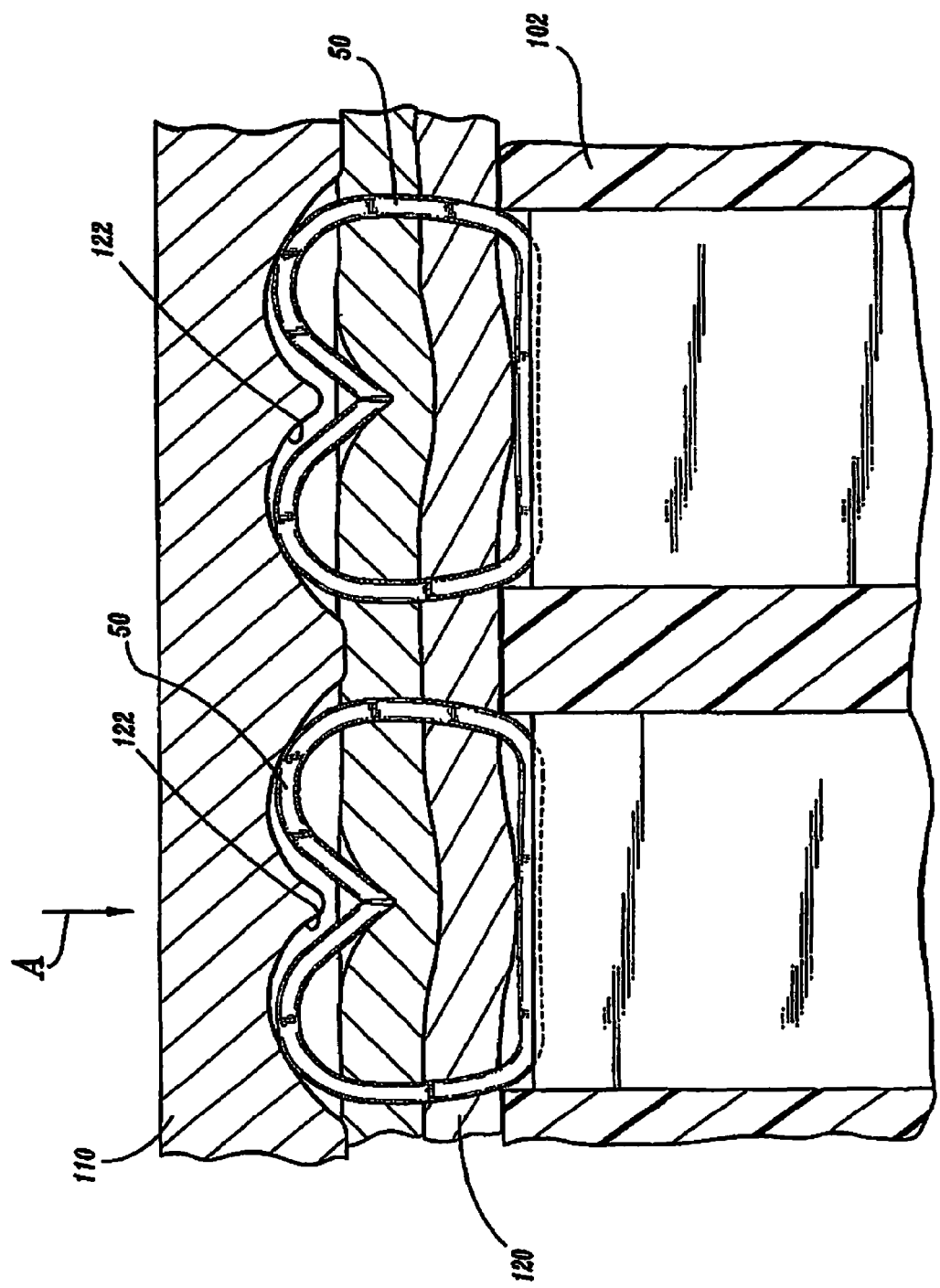

FIG. 15 illustrates a known endoscopic sequential stapler 100 including an anvil 110 and a staple cartridge 102 having novel directionally biased staples 50 loaded into the staple cartridge 102 thereof. Referring to FIGS. 16-16C, with anvil 110 and staple cartridge 102 in an open position (FIG. 16), tissue 120 is positioned between anvil 110 and cartridge 102 (FIG. 16A). Anvil 110 is now pivoted in the direction indicated by arrow "A" towards cartridge 102 (FIG. 16B) in a known manner to compress tissue 120 between anvil 110 and staple cartridge 102. Thereafter, staples 50 are ejected from staple cartridge 102 into pockets 122 formed on anvil 110. Pockets 122 deform staples 50 into a substantially B-shaped configuration (FIG. 16C). Anvil 110 can now be pivoted to the open position to permit tissue 120 to be removed from stapler 100.

Figure 17:
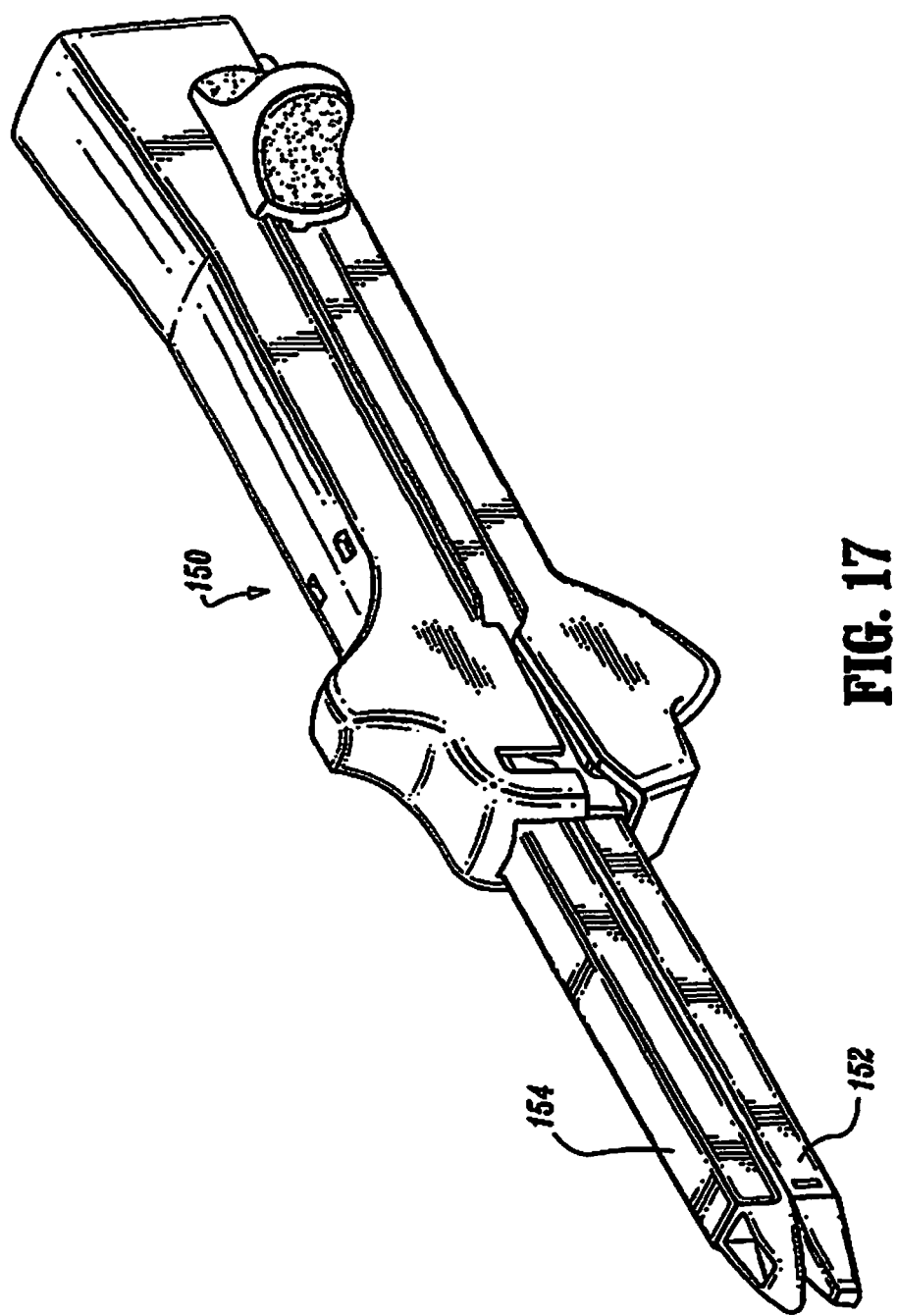
FIG. 17 is a perspective view of a gastrointestinal anastomosis-type device for firing the staple of FIG. 5.

FIG. 17 illustrates a known open type sequential stapler 150 including an anvil 152 and a staple cartridge 154 having novel directionally biased staples loaded therein. Ejection of staples from stapler occurs in a manner similar to that disclosed in FIGS. 16-16C and will not be discussed in further detail herein.

Figure 18A:
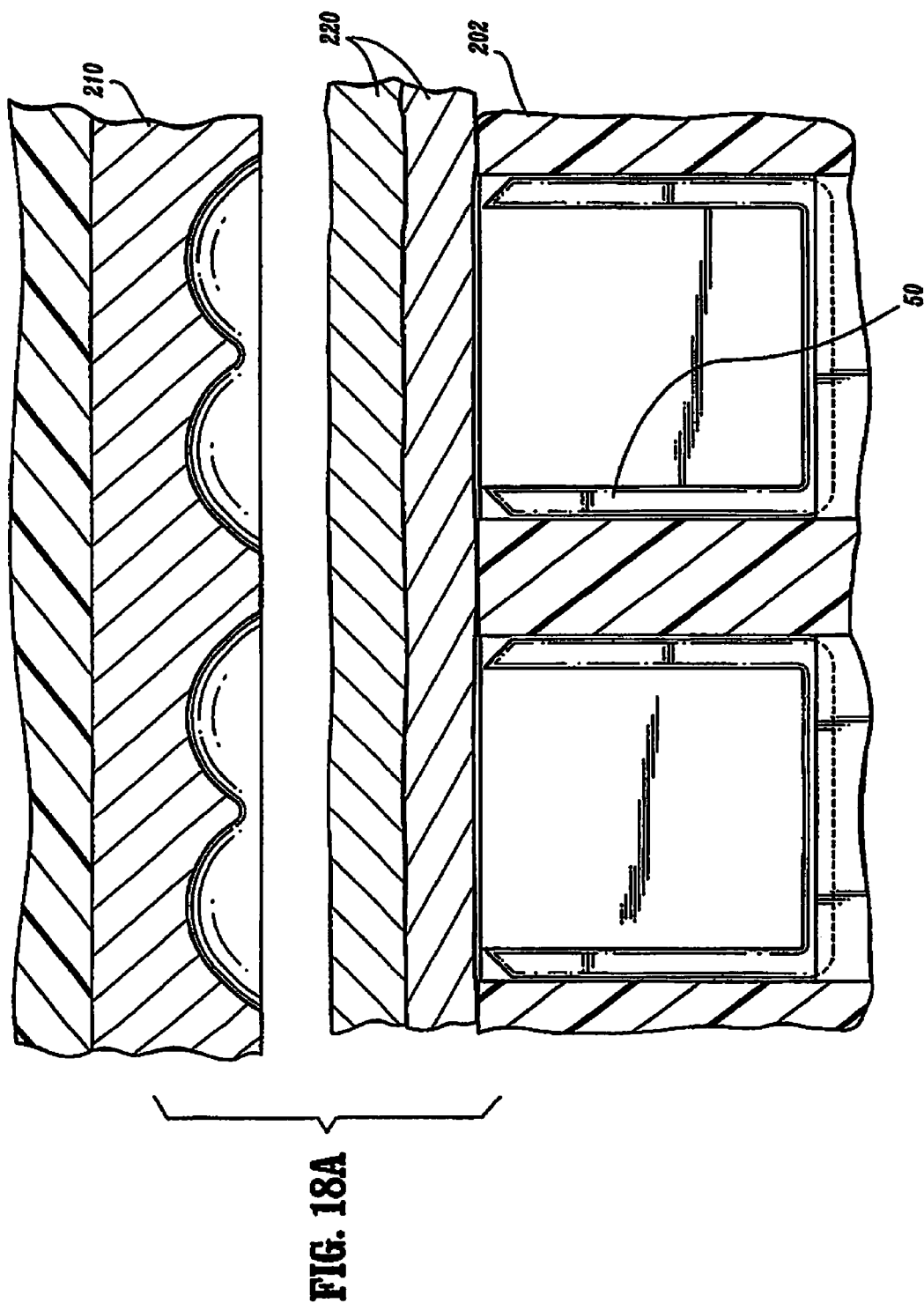
FIG. 18A is an enlarged view of the staple forming anvil and a portion of the disposable loading unit of the device of FIG. 18.
Figure 18B:
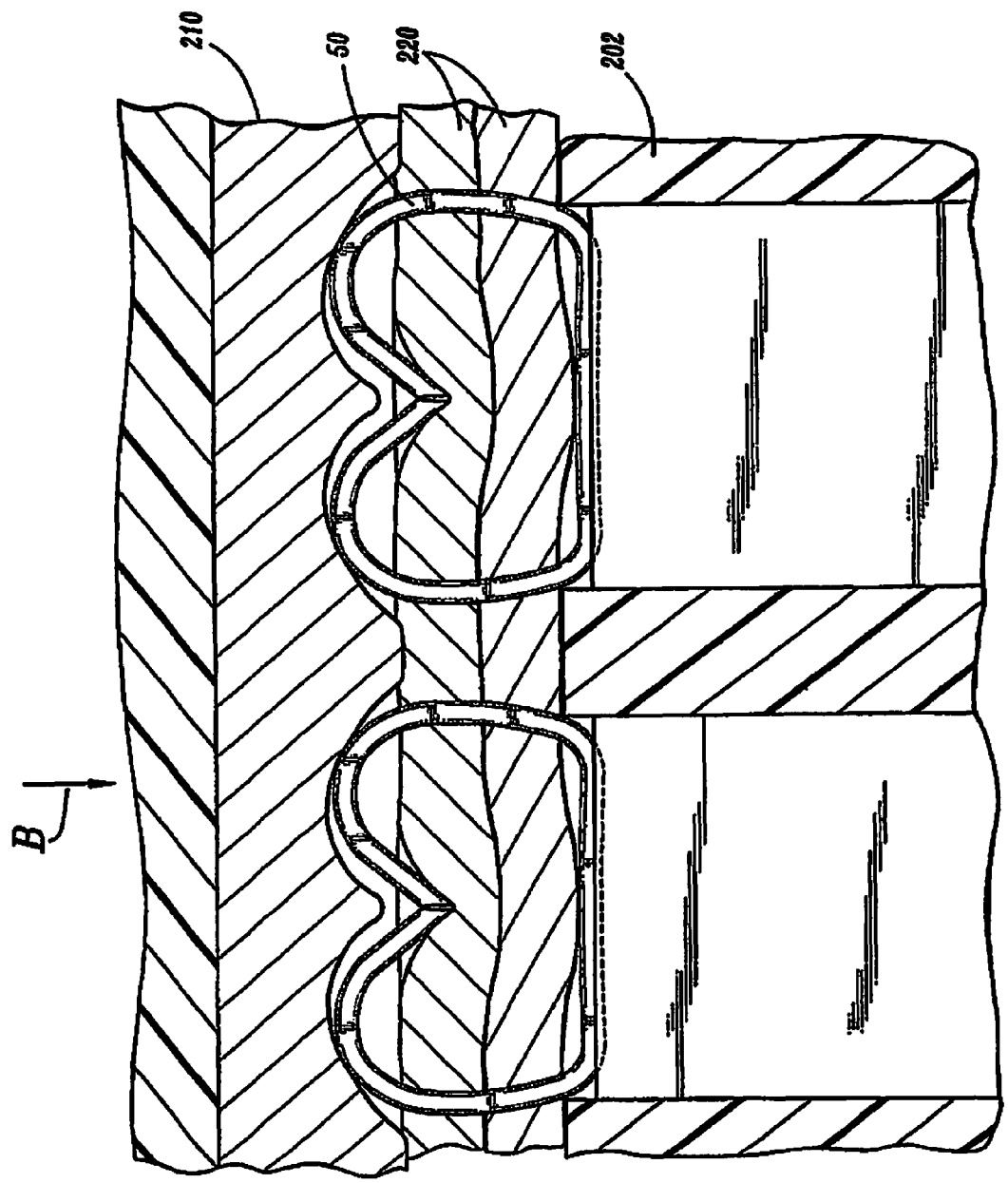
FIGS. 18B and 18C are enlarged views showing the staple formation by the anvil pockets of the instrument of FIG. 18A.
Figure 18C:
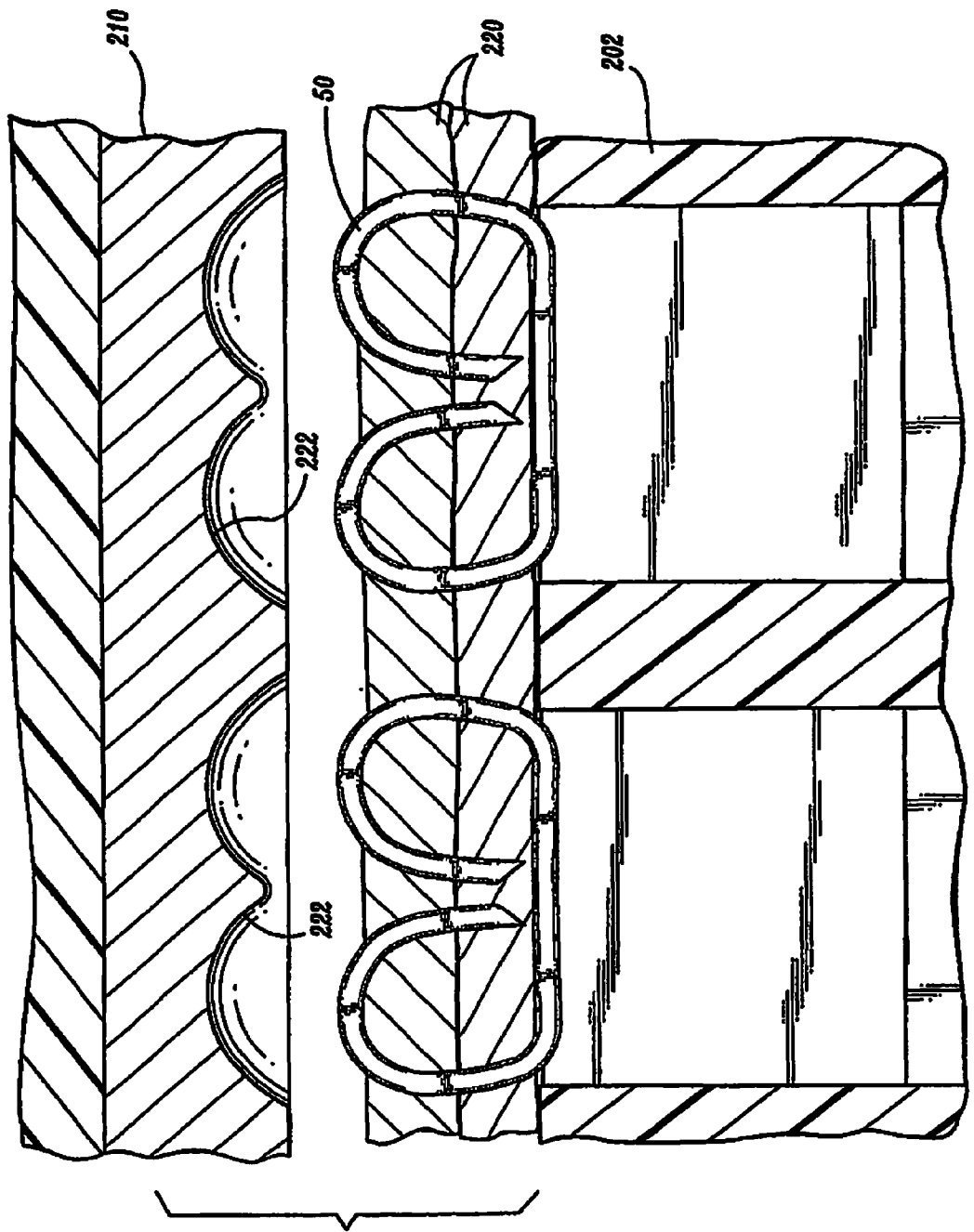

FIG. 18 illustrates a known transverse type surgical stapler 200 including an anvil 210 and a staple cartridge 202 having novel directionally biased staples 50 loaded into the staple cartridge 202. Referring to FIGS. 18A-18C, with anvil 210 and staple cartridge 202 in an open position, tissue 220 is positioned therebetween (FIG. 18A). Anvil 210 is now moved in the direction indicated by arrow "B" to an approximated position towards cartridge 202 (FIG. 18B) in a known manner to compress tissue 220 between anvil 210 and staple cartridge 202. Thereafter, staples 50 are ejected from staple cartridge 202 into pockets 222 formed on anvil 210. Pockets 222 deform staples 50 into a substantially B-shaped configuration (FIG. 18C). Anvil 210 can now be moved to the open position to permit tissue 220 to be removed from stapler 200.

Figure 19:
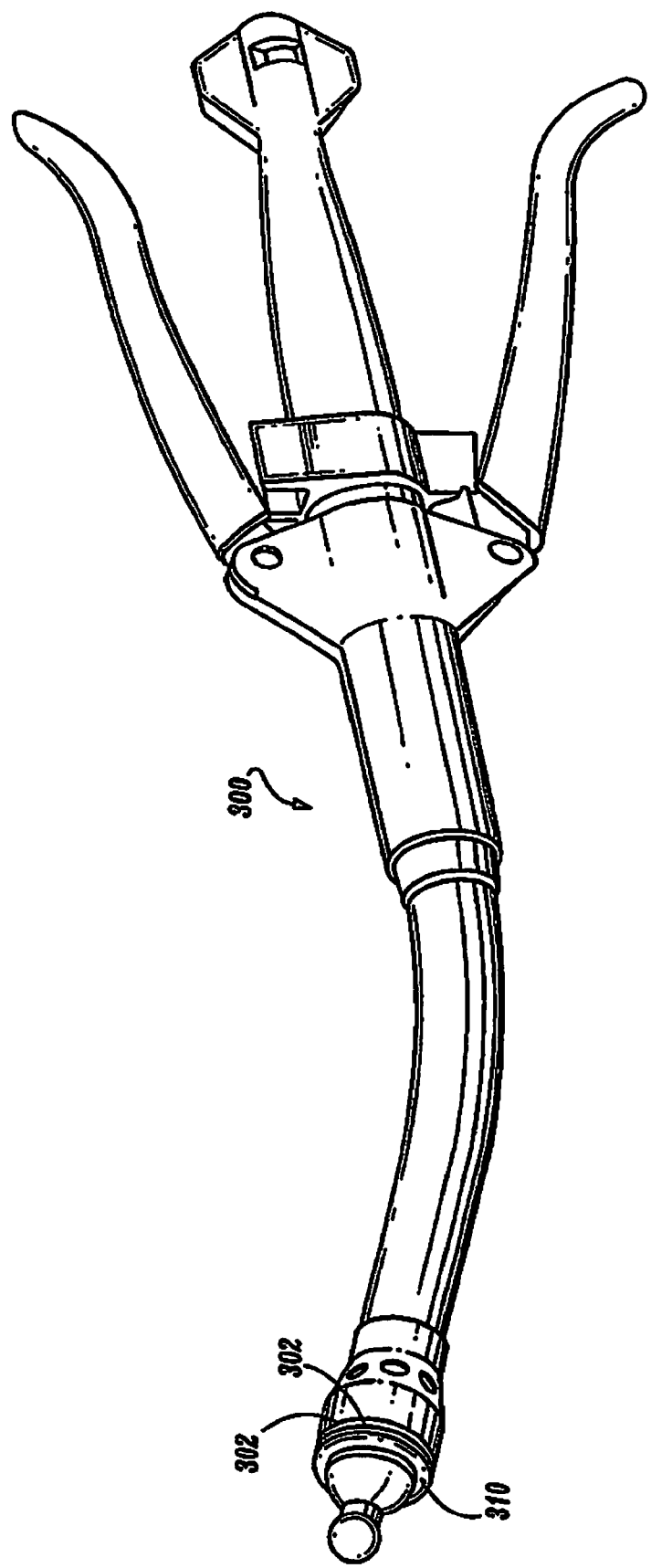
FIG. 19 is a perspective view of a circular anastomosis-type device for firing the staple of FIG. 5.
Figure 19A:
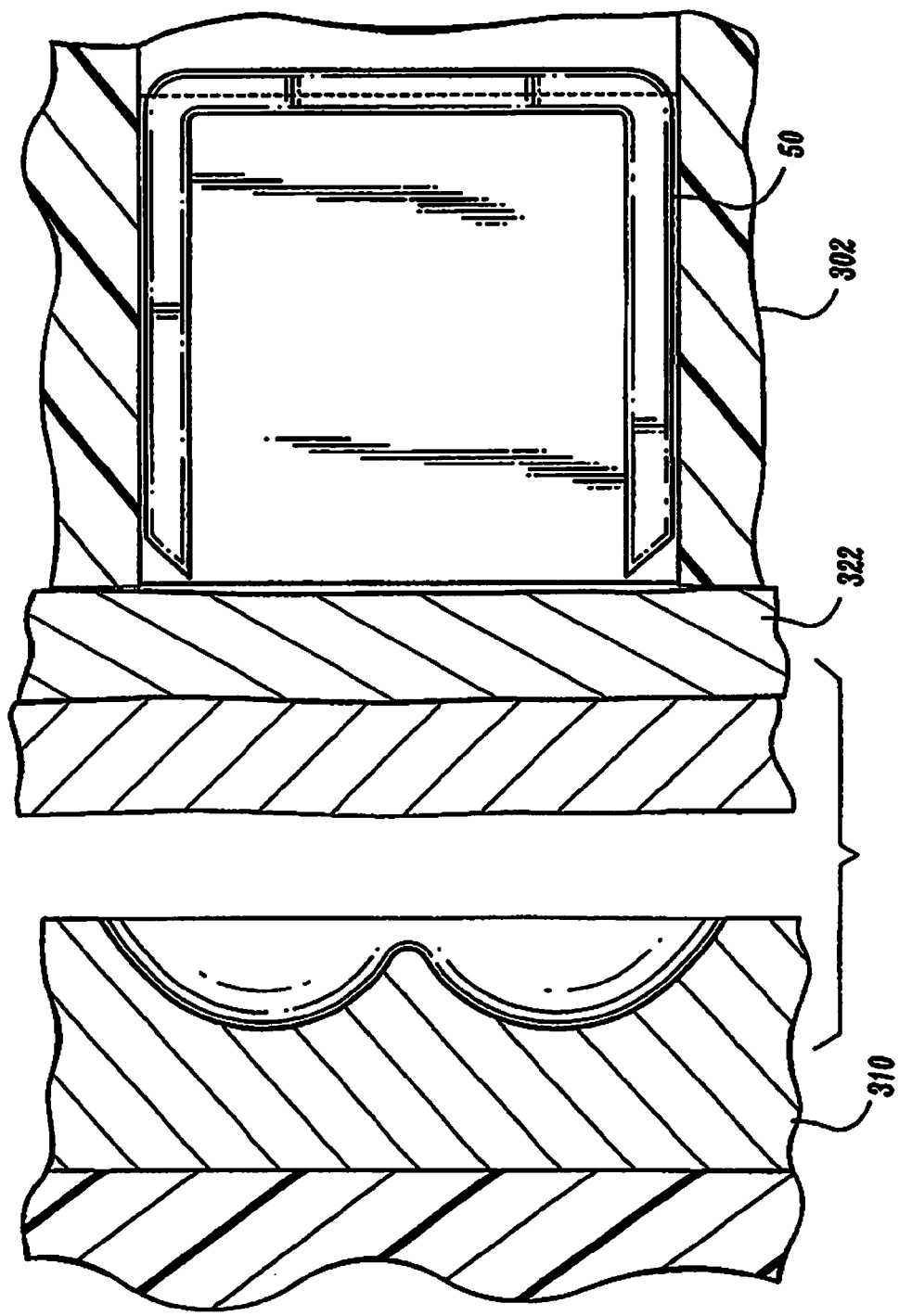
FIG. 19A is an enlarged view of the staple forming anvil and a portion of the disposable loading unit of the device of FIG. 19.
Figure 20:
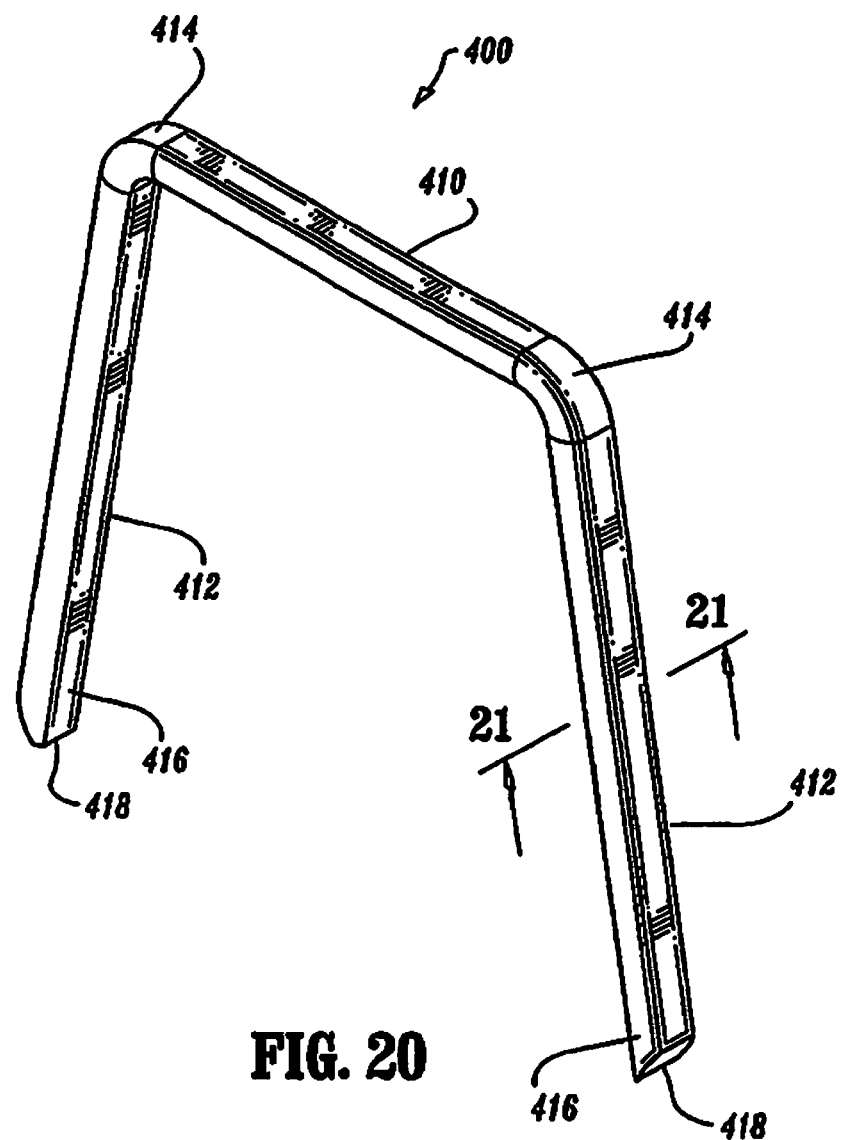
FIG. 20 is a perspective view of another embodiment of a directionally biased staple in accordance with the present disclosure.

FIG. 19 illustrates a circular stapler 300 including an anvil 310 and a staple cartridge 302 having the novel directionally biased staples 50 loaded in the staple cartridge 302. Referring to FIGS. 19A-19C, with anvil 310 and staple cartridge 302 in an open position, tissue 320 is positioned therebetween (FIG. 19A). Anvil 310 is now moved towards cartridge 302 in a known manner to compress tissue 320 between anvil 310 and staple cartridge 302 (FIG. 19B). Thereafter, staples 50 are ejected from staple cartridge 302 into pockets 322 formed on anvil 310. Pockets 322 deform staples 50 into a substantially B-shaped configuration (FIG. 19C). Anvil 110 can now be moved to the open position to permit tissue 320 to be removed from stapler 300.

Figure 21:
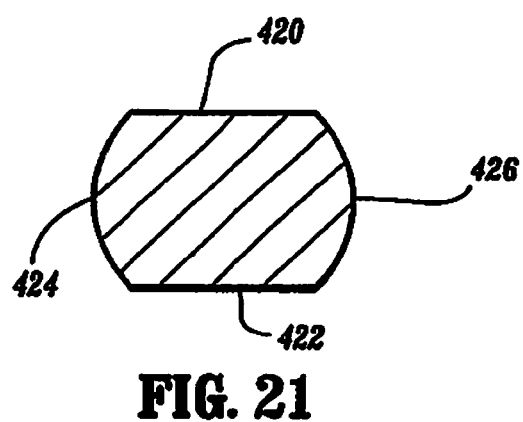
FIG. 21 is a cross-sectional view taken along section lines 21-21 of FIG. 20.
Figure 22:
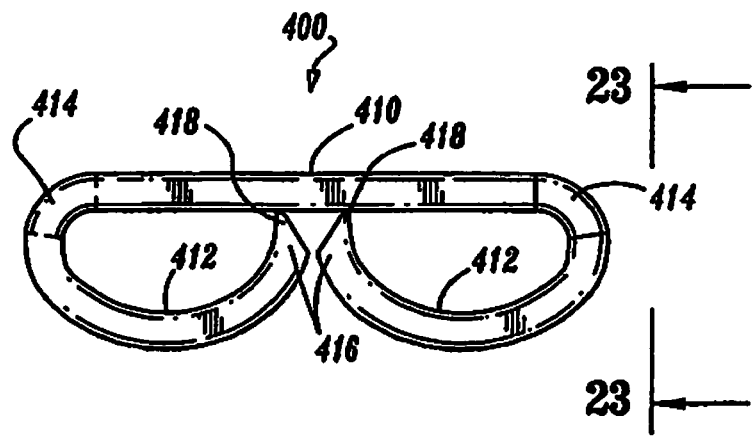
FIG. 22 is a front elevational view of the directionally biased staple shown in FIG. 20 after the staple has been deformed to the B-shaped configuration.
Figure 23:
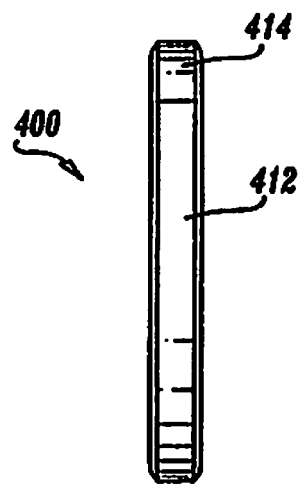
FIG. 23 is a side elevational view from the direction of lines 23-23 of FIG. 22.
Figure 24:
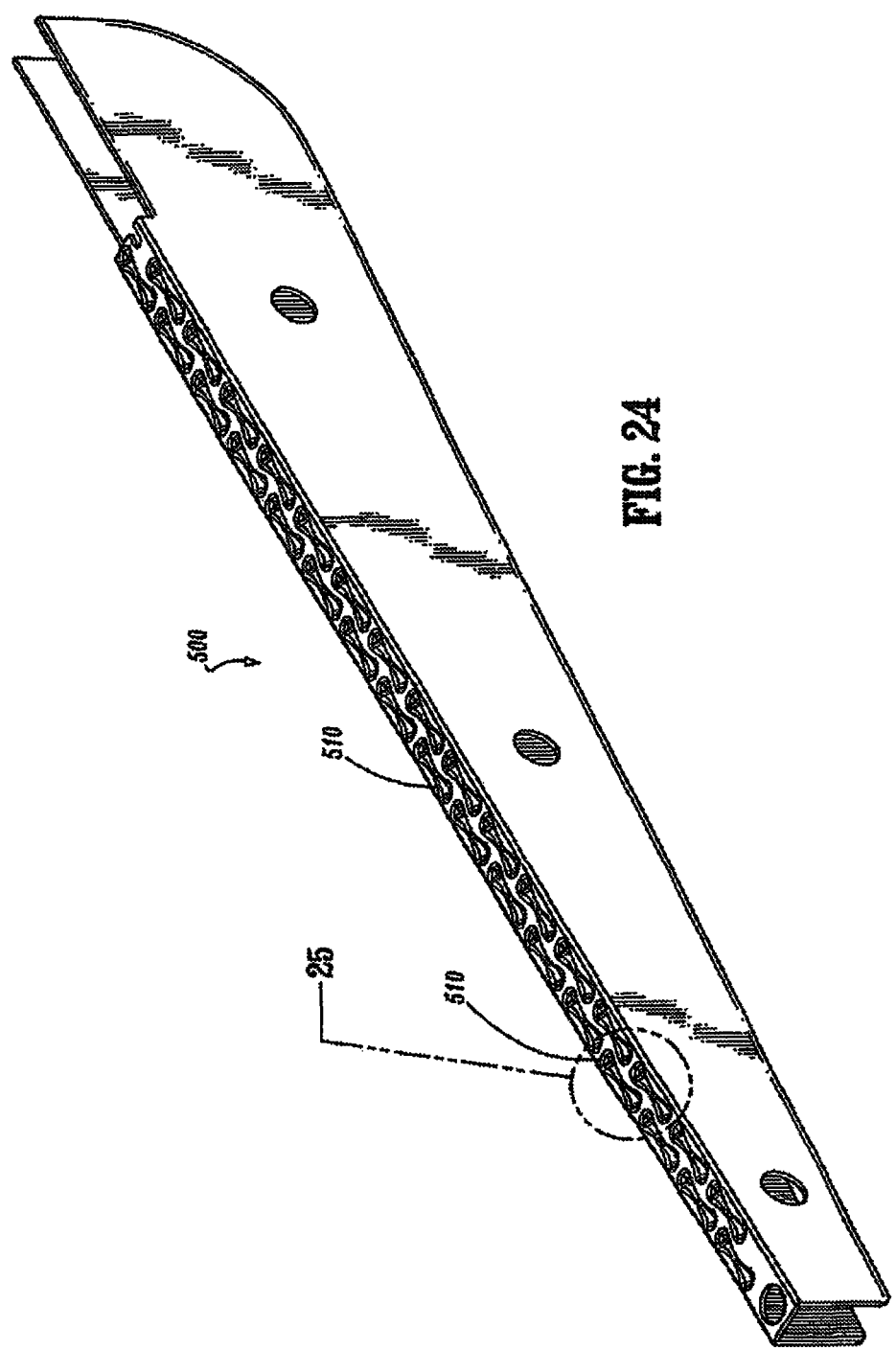
FIG. 24 is a perspective view of an anvil adapted for attachment to an endoscopic gastrointestinal anastomosis-type device.
Figure 25:
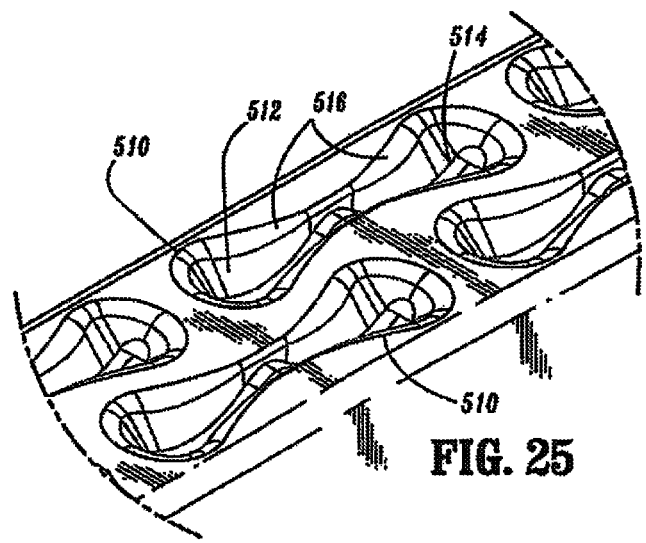
FIG. 25 is an enlarged view of the indicated area of detail shown in FIG. 24.
Figure 26:
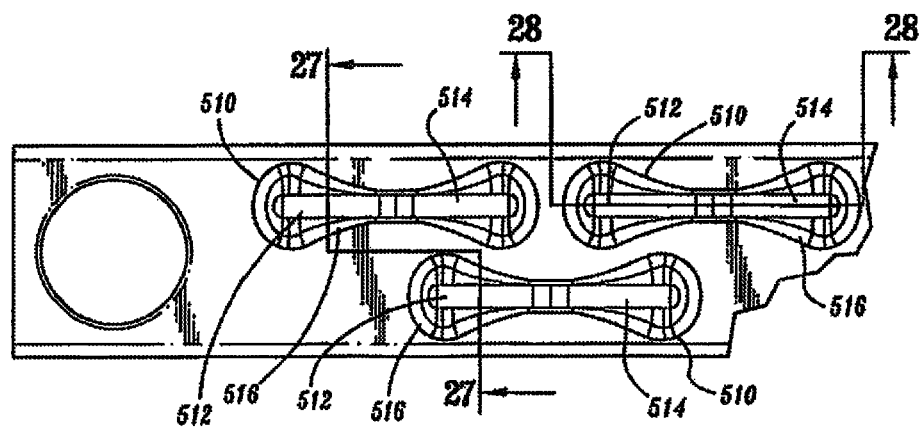
FIG. 26 is a top partial cutaway view of the anvil shown in FIG. 24.
Figure 27:
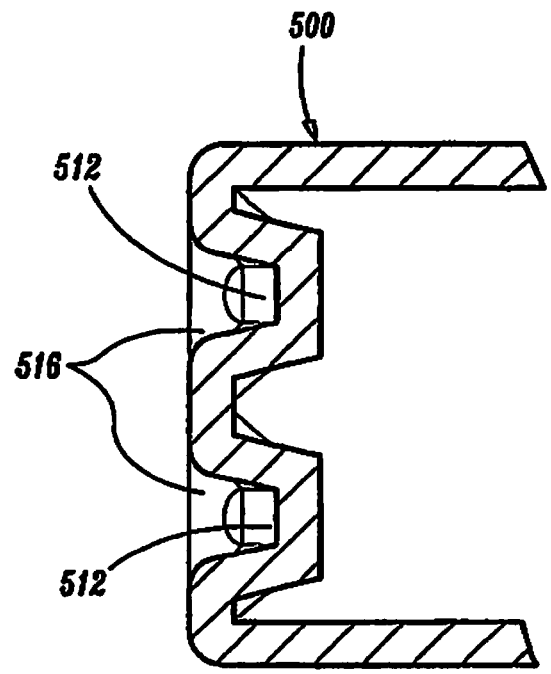
FIG. 27 is a cross-sectional view taken along section lines 27-27 of FIG. 26.
Figure 28:
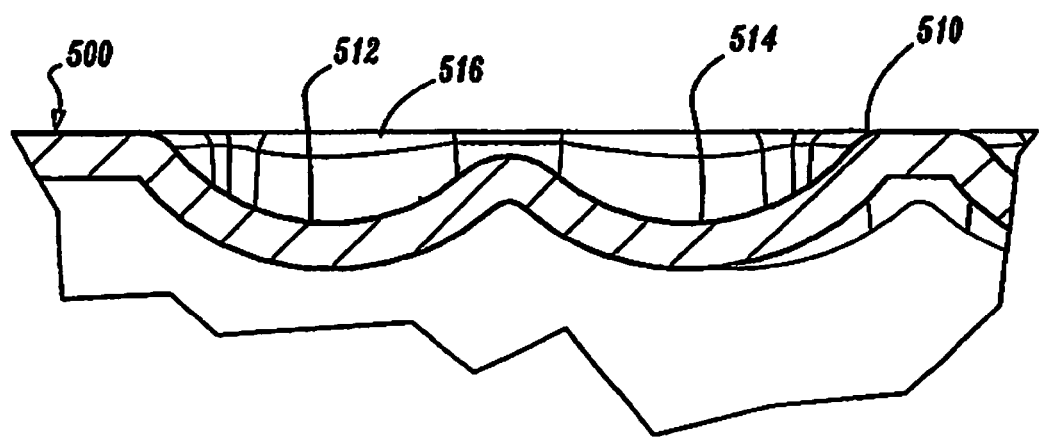
FIG. 28 is a cross-sectional view taken along section lines 28-28 of FIG. 26.

FIGS. 20-23 illustrate another preferred embodiment of the presently disclosed directionally biased staple shown generally as 400. Directionally biased staple 400 includes a crown portion 410 and a pair of outwardly angled legs 412 with a bending region 414. Legs 412 define an angle about 5" to about 15" with crown portion 410. Preferably, legs 412 define an angle of about 9" with respect to crown portion 410. Alternately, other angle orientations are envisioned. The angle of legs 412 function to retain the staple within staple receiving slots of a staple cartridge prior to use, i.e., legs 412 frictionally engage the slot walls of a staple cartridge to retain the staple within a cartridge slot. Tissue penetrating portions 416 are formed at the distal end of legs 412 and preferably have a chisel shape with points 418 adjacent inner facing sides of legs 412. Referring to FIG. 21, staple 400 has a cross-section having flat top and bottom surfaces 420 and 422 and semi-circular side surfaces 424 and 426. Preferably, this cross-section is achieved by rolling top and bottom surfaces of wire stock. Alternately, other methods including extrusion and coining may be used to form staple 400. Using the appropriate formulas, the Moment of Inertia ratio of staple 400 is approximately 2. Alternately, the dimensions of staple 400 may be varied in a manner to achieve a Moment of Inertia ratio within the preferred range of about 1.1 to about 3. FIGS. 22 and 23 illustrate staple 400 in the formed state wherein staple 400 assumes a B-shaped configuration.

There are various methods of manufacturing the surgical staple. For example, the method could include the steps of flat rolling the wire stock to form at least one flat surface thereon and cutting a length of round wire stock to a predetermined length corresponding to a desired length of a finished staple or extruding the stock with a flat surface. The stock is bent into a form having a backspan and a pair of legs wherein the staple has an aspect ratio of between about 1.1 to about 3.0.

FIGS. 24-28 illustrate an anvil 500 which is configured for attachment to a transverse-type surgical stapler such as shown in FIG. 18. Anvil 500 includes a plurality of staple pockets 510 formed in the surface of the anvil. Each staple pocket 510 includes first and second staple forming cups 512 and 514 and a channeling surface 516 disposed around each of the staple forming cups. An anvil including such a staple forming pocket has been disclosed in U.S. Pat. No. 5,480,089 filed Aug. 19, 1994, the entirety of which is incorporated herein by reference. Anvil 500, including staple forming cups 512 and 514 and channeling surface 516 can be adapted for use with any of the surgical stapling devices described in the specification above including endoscopic gastrointestinal anastomosis-type devices (FIG. 15), gastrointestinal anastomosis-type devices (FIG. 17), transverse anastomosis-type devices (FIG. 18) and circular anastomosis-type devices (FIG. 19). U.S. patent application Ser. No. 09/687,815, filed Oct. 13, 2000, now U.S. Pat. No. 6,817,508, discloses a transverse anastomosis-type device including such an anvil assembly. This application is incorporated herein in its entirety by reference.

Figure 29:
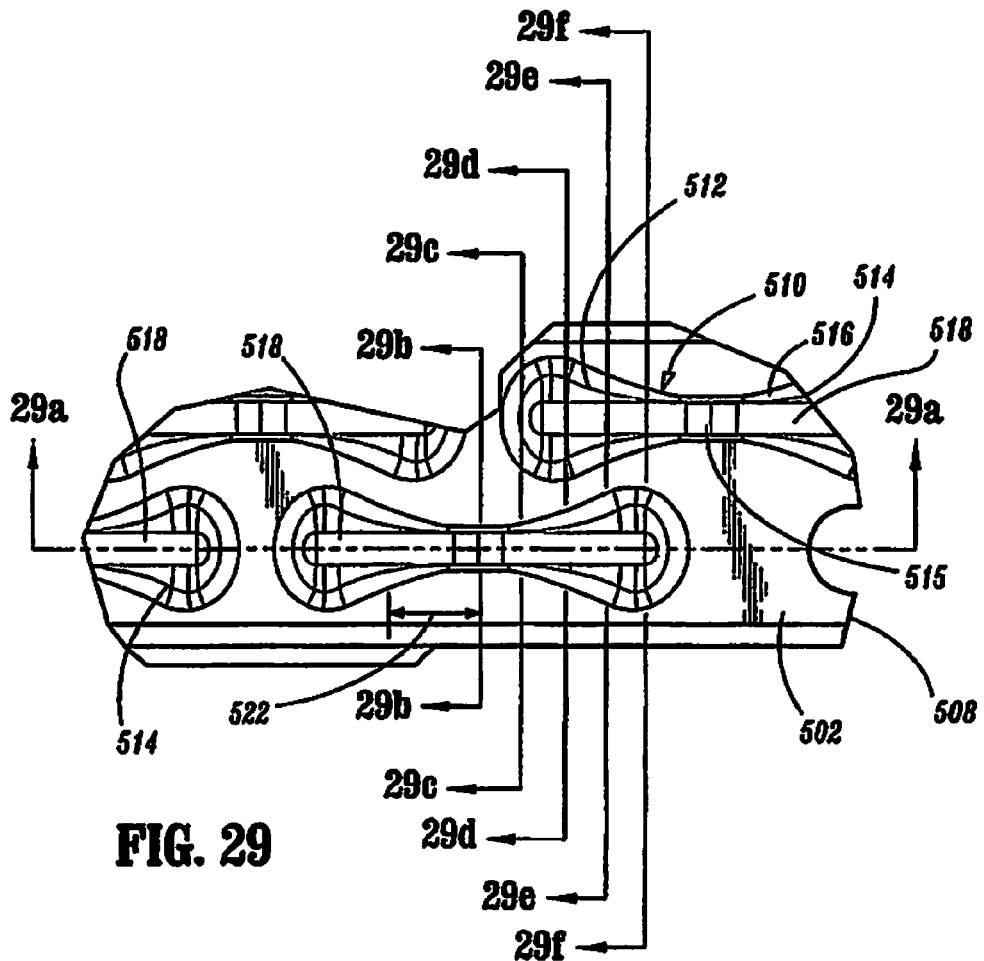
FIG. 29 is another enlarged top view of a portion of the anvil assembly shown in FIG. 25.
Figure 29A:
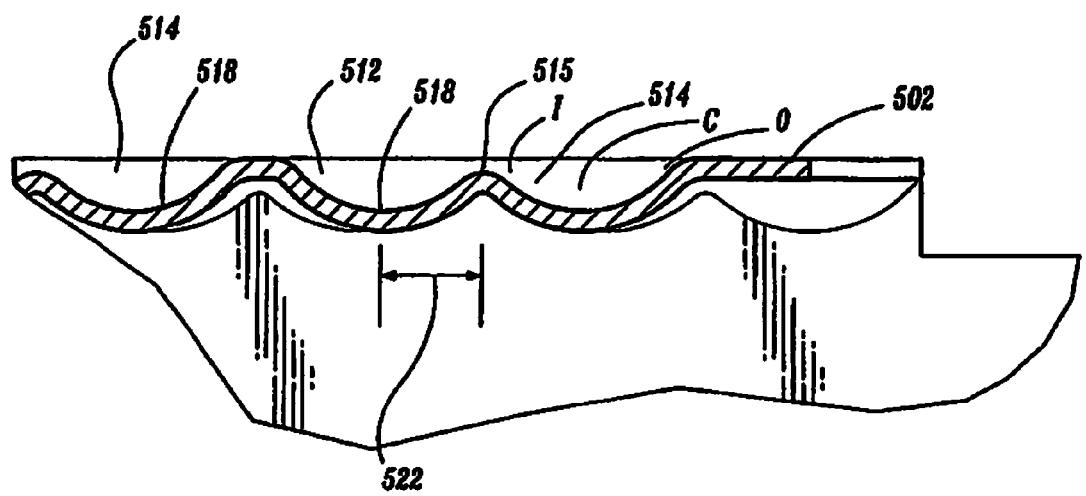
FIG. 29a is a cross-sectional view taken along section lines 29a-29a of FIG. 29.
Figure 29B:
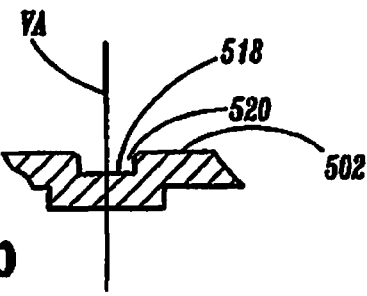
FIG. 29b is a cross-sectional view taken along section lines 29b-29b of FIG. 29.
Figure 29C:
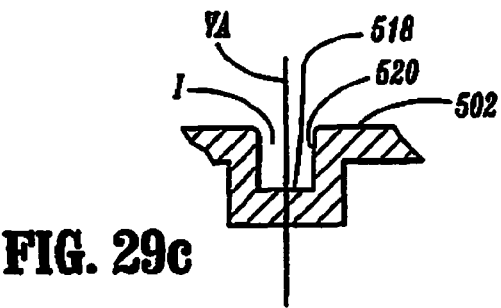
FIG. 29c is a cross-sectional view taken along section lines 29c-29c of FIG. 29.
Figure 29D:
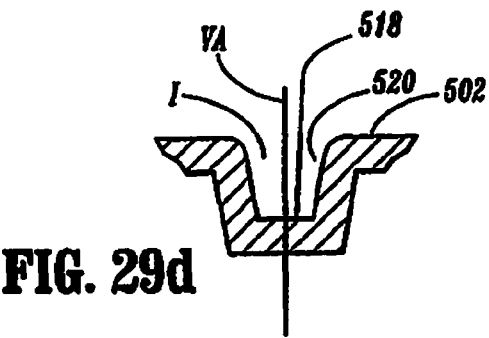
FIG. 29d is a cross-sectional view taken along section lines 29d-29d of FIG. 29.
Figure 29G:
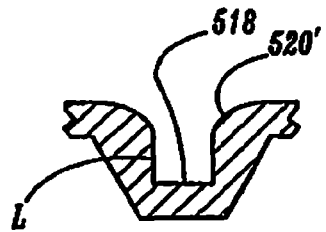
FIG. 29g is an alternative embodiment of the cross-sectional view taken along section lines 29c-29c of FIG. 29.
Figure 29E:
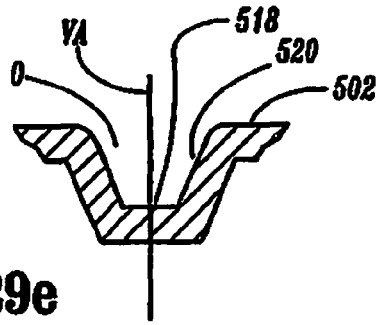
FIG. 29e is a cross-sectional view taken along section lines 29e-29e of FIG. 29.
Figure 29F:
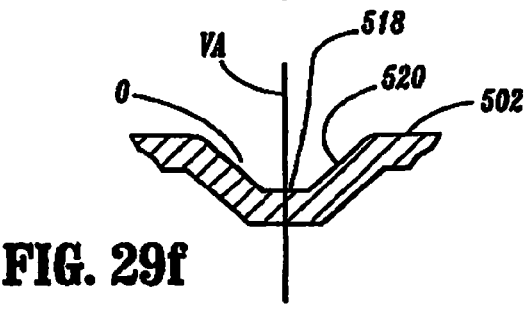
FIG. 29f is a cross-sectional view taken along section lines 29f-29f of FIG. 29.

FIGS. 29-29f illustrate in greater detail anvil assembly 500 shown in FIGS. 24-28. Anvil assembly 500 includes an anvil plate 508 defining a tissue contact surface 502 and having a plurality of staple pockets 510 formed in surface 502 of the anvil plate 508. As discussed above, each staple pocket 510 includes first and second staple forming cups 512 and 514 and a channeling surface 516 formed about at least a portion (preferably the majority) of each of the staple forming cups 512 and 514. Each staple forming cup 512 and 514 is defined by sidewalls 520 and an elongated base surface 518. As shown in FIG. 29a each staple forming cup 512, 514 includes an outside portion O, a central portion C, and an inside portion I. Outside portion O extends from the outer extent of the forming cup (shown in FIG. 29f) to central portion C of the forming cup at and about the deepest portion of the forming cup (see the ends of lead lines of reference numbers 512 and 514 in FIG. 28). Inside portion I of each forming cup extends from central portion C of the forming cup to the highest operative staple leg or tip engaging point at or near apex 515 of each pocket 510 (See FIG. 29a). Base surface 518 extends axially from adjacent the outer extent of the outside portions of each of the staple forming cups 512 and 514, as shown in FIG. 29f, through the central and inside portions of each of the staple forming cups 512 and 514 and terminates at or near the apex 515 of pocket 510 (e.g., see FIG. 29a).

Elongated base surface 518 is substantially linear, i.e., substantially flat (herein understood to include flat), along its transverse axis and is concavely or curved along its longitudinal axis. The substantially linear surface preferably corresponds to the shape of the points of a staple to be formed thereagainst. Since the preferred staple has substantially linear tips (See staple 400 in FIGS. 20-22), the preferred base surface for such a staple is substantially linear. This provides line-to-line contact between the flat surfaces of the staple tips and the substantially linear base surface. By providing a base surface having a shape that corresponds to the shape of the staple point, friction is reduced and galling of the staple tip during staple formation is minimized. The shape of base surface 518 may be altered to conform to the shape of the staple points of different staples, which may be rounded, triangular, etc.

Figure 30:
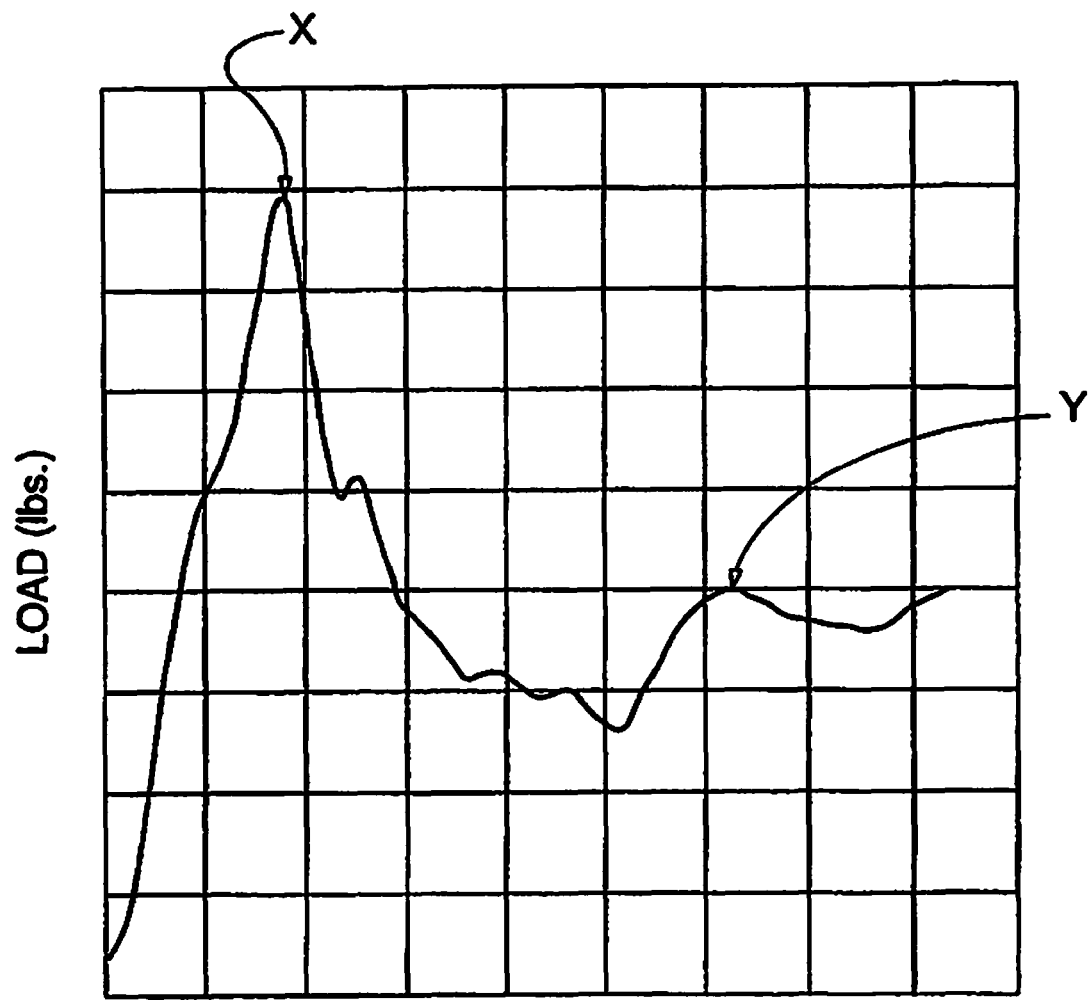
FIG. 30 is a graph illustrating force vs. deformation of a staple being formed in a pocket of the anvil shown in FIG. 24.

In the preferred embodiment shown, sidewalls 520, which partly define staple forming cups 512 and 514, are angular as they extend from the lower portion of the channeling surface to base surface 518. Side walls 520 gradually become progressively more vertical (or perpendicular in relation to tissue contact surface 502) along elongated base surface 518 starting from the outer extent of outside portion O of cups 512 and 514 where sidewalls 520 are widely angular [relative to tissue contact surface 502 or to the vertical axis VA of the pocket (FIG. 30f)] towards and through central portion C and inside portion I of cups 512 and 514. Preferably, the central and inside portions of cups 512 and 514 are defined by substantially vertical (herein understood to include vertical) sidewalls 520, such that a substantially vertical trap 522 is formed at least in the central and inside portions of each staple forming cup. The substantially vertical trap can start at any suitable location along the longitudinal axis of staple forming cup 512, 514 (FIG. 30). While it is preferred that the trap begin in outside portion O of the staple forming cup before or when the first peak force occurs (FIG. 30), properly formed staples in accordance with the invention can also be obtained when the substantially vertical trap starts in the central or inside portion of the staple forming cup. Briefly, substantially vertical trap 522 functions to align and accurately form staples therein. The substantially vertical trap can be of any suitable length depending on, for example, the dimensions and configuration of the particular staple and staple forming cup, and the desired configuration of the finished staple. The length of substantially vertical trap 522 is preferably between about 0.5r and about 2r, where r is the radius of curvature of each pocket, and more preferably, the length of the vertical trap is about r. A preferred radius r is from about 0.030 inch to about 0.100 inch, more preferably about 0.050 inch, herein understood to include 0.054 inch.

Referring to FIG. 30, as a staple is formed against an anvil, the force applied to the staple typically will increase as the staple moves into the staple pocket until the force is sufficient to buckle or plastically deform the staple. This peak force applied to the staple is schematically illustrated in the graph shown in FIG. 30 by the letter AX@ and typically occurs first when the tips of the legs of a staple engage base surface 518 in the outside portion of cups 512 and 514, where the legs begin to plastically deform. The first peak force typically occurs when the tips of the staple legs strike base surface 518 and move approximately between the positions shown in FIGS. 10B and 10C. A second peak force identified by the letter AY@ in the graph shown in FIG. 30 is applied to the staple to bend the staple legs upwardly. The second peak force Y typically occurs when a portion of the legs of the staple is positioned in engagement with base surface 518, also in outside portion O, of cups 512 and 514 approximately between the positions shown in FIGS. 10D and 10E. Staple pockets 510 of anvil assembly 500 are preferably configured as a trough that preferably gradually funnels and directs movement of the staple tips and legs of a staple being formed into the substantially vertical trap at least by the time peak forces X and Y are reached. The substantially vertical trap captures the tips and the legs of the staples within and along the trap, preferably including during the peak loads of staple formation. Capturing the tip and legs of a staple herein means that at least a portion, preferably the base portion, of the sidewalls of the substantially vertical trap of the staple forming cup closely confines the staple tips and legs in a slip fit relationship to minimize lateral or transverse movement of the tips and legs and positively direct the staple through the substantially vertical trap portion of the staple forming cup. By doing so, malformation by misalignment or twisting of the staple is minimized or eliminated.

FIGS. 29b-29f show that side walls 520 with base surface 518 form a trough that gradually funnels the tips and legs of a staple from outside portion O of cups 512 and 514 into a substantially vertical trap in the outside, central and inside portions O, C and I, respectively, of the cups, and terminates at or near apex 515 of cups 512 and 514.

FIG. 29f shows that the outside portion O of staple forming cup 514 is widely angled relative to tissue forming surface 502 or vertical axis VA to provide a large target area to receive the tips of the staple legs as they are fired into anvil pocket 510.

FIG. 29e, also taken through outside portion O of forming cup 514, shows that sidewalls 520 are at a sharper angle relative to vertical axis VA to more closely guide the staple tips and legs along forming cup 514.

FIG. 29d shows that the sidewalls 520 along inside portion I, although at an angle of about 8°, are substantially vertical relative to vertical axis VA. In FIGS. 29c and 29b, the sidewalls are shown as vertical. Ideally and most preferably a major portion of sidewalls 520 of the substantially vertical traps are actually vertical. It is to be understood that in attempting to obtain a vertical sidewall, whether the sidewalls are actually vertical or are substantially vertical may depend on how the anvil pockets are formed. Preferably, for economic reasons and ease of manufacture, the anvil is formed from a thin sheet of metal and the pockets are stamped therein. Since there is some spring back, i.e., elastic deformation, during cup formation by stamping, the sidewalls of the cups will in some instances actually be substantially vertical. If the anvil is cast or machined, the sidewall typically truly will be vertical. Thus, in accordance with the invention, the object is to provide a trough that funnels and guides the staple tips and legs into an elongated substantially vertical trap that traps or captures and positively directs the staple tips and the legs within and along the substantially vertical trap in its path to or near the apex as the staple is formed. While it is preferred that the sidewalls of the staple forming cups that lead to the substantially vertical trap be angular, such is not essential. Such sidewalls and/or upper portions of the sidewalls along the substantially vertical trap can be arcuate (520', FIG. 29g) or otherwise shaped, so long as enough of the height of the or a lower portion, e.g., "L", of the sidewalls of the substantially vertical trap are substantially vertical in order to trap the staple in accordance with the invention. It is contemplated that "enough of the height of the or a lower portion of the sidewall" means that the height is at least about ½ of the thickness or diameter of the particular staple being formed. It is contemplated that substantially vertical sidewalls are those that are less than about 20° relative to the vertical axis, preferably less than about 15° and more preferably less than about 10°.

While the parameters of the start, length, configuration and end of the vertical trap and the substantially vertical disposition of the sidewalls has been attempted to be explained, it is understood that these parameters can vary depending on various factors, for example, the starting staple configuration and its dimensions and desired final shape, so long as the principle of capturing the tips and legs of a staple in a substantially vertical trap is present or employed to capture and positively and direct the movement and direction of the staple to optimize proper staple formation.

The employment of substantially vertical traps in staple forming cups, especially those having a substantially linear base surface is especially advantageous for use in connection with the directionally biased staples disclosed herein, particularly those having substantially linear tips. This combination is particularly effective in compensating for variations in the staple manufacturing and forming systems to minimize the occurrence of malformed staples, including those malformed because of variations in the density of the tissue to be stapled, in staple shape, geometry, or material, and in the configuration of the staple tips, e.g., uneven angular or rounded.

Although specific embodiments of the present disclosure have been described above in detail, it will be understood that this description is merely for purposes of illustration. Various modifications of and equivalent structures corresponding to the disclosed aspects of the preferred embodiment in addition to those described above may be made by those skilled in the art without departing from the spirit of the present disclosure which is defined in the following claims, the scope of which is to be accorded the broadest interpretation so as to encompass such modifications and equivalent structures.

What is claimed is:

1. An anvil assembly for use with a surgical stapler, the anvil assembly comprising:
    a tissue contact surface;
    a plurality of staple pockets formed in the tissue contact surface, each of the plurality of staple pockets defining a longitudinal axis; and
    each of the plurality of staple pockets including first and second staple forming cups, each of the first and second staple forming cups having an outside portion and an inside portion, the inside portion of the first and second staple forming cups being positioned in close relation to each other and joined by a central portion therebetween, the outside portion of the first and second staple forming cups being positioned in spaced relation to each other, each of the first and second staple forming cups being defined by sidewalls and an elongated base surface extending within the first and second staple forming cups and the central portion therebetween;
    wherein the sidewalls have a linear profile extending to upper portions of the sidewalls, the upper portions of the sidewalls having an arcuate contoured profile that gradually approaches the tissue contact surface to form a line of intersection,
    wherein the line of intersection extends along the tissue contact surface to define a first curved portion bordering the upper portion of the sidewall of the first staple forming cup, a central portion and a second curved portion bordering the upper portion of the sidewall of the second staple forming cup, and
        wherein the central portion extends between the first curved portion of the line of intersection and the second curved portion and wherein the central portion defines two parallel lines defining the respective upper portions of the sidewalls extending along a portion of the tissue contact surface, the sidewalls extending along the central portion and beneath the tissue contact surface to the elongated base surface defined in the central portion that joins the first staple forming cup and the second staple forming cup.

2. The anvil assembly of claim 1, wherein the arcuate contoured upper portions of the sidewalls are defined in a plane orthogonal to the tissue contact surface.

3. The anvil assembly of claim 1, wherein the elongated base surface of each of the first and second staple forming cups is substantially linear along each of a plurality of transverse axes extending orthogonally horizontally to the respective longitudinal axis defined by the plurality of staple pockets.

4. The anvil assembly of claim 1,
    wherein the elongated base surface extends along each of the plurality of staple pockets,
    wherein the elongated base surface of each of the first and second staple forming cups includes a transverse surface disposed substantially perpendicular to the longitudinal axis, and
    wherein the transverse surface is linear along the majority of its length.

5. The anvil assembly of claim 1 wherein the sidewalls of each of the first and second staple forming cups form an acute angle with respect to the tissue contact surface of the anvil assembly at an outside portion of each of the first and second staple forming cups.

6. A surgical stapler comprising:
    a staple cartridge having a plurality of directionally biased staples contained therein and pushers to advance the staples; and
    an anvil assembly comprising:
        a tissue contact surface;
        a plurality of staple pockets formed in the tissue contact surface, each of the plurality of staple pockets defining a longitudinal axis; and
        each of the plurality of staple pockets including first and second staple forming cups, each of the first and second staple forming cups having an outside portion and an inside portion, the inside portion of the first and second staple forming cups being positioned in close relation to each other and joined by a central portion therebetween, the outside portion of the first and second staple forming cups being positioned in spaced relation to each other, each of the first and second staple forming cups being defined by sidewalls and an elongated base surface extending within the first and second staple forming cups and the central portion therebetween;
        wherein the sidewalls have a linear profile extending to upper portions of the sidewalls, the upper portions of the sidewalls having an arcuate contoured profile that gradually approaches the tissue contact surface to form a line of intersection,
        wherein the line of intersection extends along the tissue contact surface to define a first curved portion bordering the upper portion of the sidewall of the first staple forming cup, the central portion and a second curved portion bordering the upper portion of the sidewall of the second staple forming cup, and
        wherein the central portion extends between the first curved portion of the line of intersection and the second curved portion and wherein the central portion defines two parallel lines defining the respective upper portions of the sidewalls extending along a portion of the tissue contact surface, the sidewalls extending along the central portion and beneath the tissue contact surface to the elongated base surface defined in the central portion that joins the first staple forming cup and the second staple forming cup.

7. The surgical stapler of claim 6, further comprising a handle assembly and an elongated portion extending between the handle portion and the staple cartridge, the elongated portion defining a second longitudinal axis, wherein the staples are advanced toward the anvil assembly in a direction along the second longitudinal axis.

8. The surgical stapler of claim 6, further comprising a handle assembly and an elongated portion extending between the handle portion and the staple cartridge, the elongated portion defining a second longitudinal axis, wherein the staples are advanced toward the anvil assembly in a direction transverse to the second longitudinal axis.

9. The surgical stapler of claim 6, wherein the arcuate contoured upper portions of the sidewalls are defined in a plane orthogonal to the tissue contact surface.

10. The surgical stapler of claim 6, wherein the staples are non-circular in cross section.

11. The surgical stapler of claim 10, wherein the staples are oval in cross-section.

12. The surgical stapler of claim 10, wherein the staples are trapezoidal in cross-section.

13. The surgical stapler of claim 10, wherein the staples are elliptical in cross-section.

14. The surgical stapler of claim 10, wherein the staples are rectangular in cross-section.

15. The surgical stapler of claim 10, wherein the staples are triangular in cross-section.

16. The surgical stapler of claim 15, wherein the staples are scalene triangular in cross-section.

17. The surgical stapler of claim 10, wherein the staples are substantially oval with linear sides in cross-section.

18. The surgical stapler of claim 10, wherein the staples form an inverse trapezoidal shape in cross-section.

\* \* \* \* \*